United States Patent
Castelli et al.

(10) Patent No.: US 12,329,916 B2
(45) Date of Patent: Jun. 17, 2025

(54) CATHETER HANDLE WITH TORQUE MECHANISM AND VALVE RELIEF COMPONENT

(71) Applicant: MEDTRONIC, INC., Minneapolis, MN (US)

(72) Inventors: Brian Castelli, Rohnert Park, CA (US); Ashley Spink, Bellingham, WA (US); William Berthiaume, Santa Rosa, CA (US); William Chang, Santa Rosa, CA (US); Victoria Ung, Santa Rosa, CA (US); James Mitchell, Windsor, CA (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

(21) Appl. No.: 17/897,663

(22) Filed: Aug. 29, 2022

(65) Prior Publication Data

US 2022/0409860 A1 Dec. 29, 2022

Related U.S. Application Data

(63) Continuation of application No. 16/907,466, filed on Jun. 22, 2020, now Pat. No. 11,446,470.
(Continued)

(51) Int. Cl.
*A61M 25/01* (2006.01)
*A61M 25/00* (2006.01)
*A61M 25/09* (2006.01)

(52) U.S. Cl.
CPC .... *A61M 25/0136* (2013.01); *A61M 25/0075* (2013.01); *A61M 25/0147* (2013.01);
(Continued)

(58) Field of Classification Search
CPC .......... A61M 25/0136; A61M 25/0075; A61M 25/0147
See application file for complete search history.

(56) References Cited

U.S. PATENT DOCUMENTS 4,665,918 A * 5/1987 Garza ...................... A61F 2/95
623/1.11
5,178,159 A 1/1993 Christian
(Continued)

FOREIGN PATENT DOCUMENTS

EP  616794 A1  12/1999
EP  3 398 562 B1  12/2022
(Continued)

OTHER PUBLICATIONS

International Search Report issued Dec. 10, 2020 in Intl. Appl. No. PCT/US2020/038493.

*Primary Examiner* — Nathan R Price
*Assistant Examiner* — Adam J. Cermak
(74) *Attorney, Agent, or Firm* — MEDLER FERRO WOODHOUSE & MILLS PLLC

(57) ABSTRACT

A catheter includes a handle with torqueing and steering mechanisms. The torqueing mechanism includes a rotatable nosecone and a bearing coupled to the nosecone to be rotatable therewith. The bearing is concentrically disposed over a shaft of the catheter. The steering mechanism includes a rack coupled to the bearing to be slideable therewith and a pull wire having a proximal end attached to the bearing and a distal end attached to a distal portion of the shaft. Rotation of the nosecone causes an entire length of the shaft to rotate and axial movement of the rack tensions the pull wire to bend the distal portion of the shaft. A valve relief component is slidingly disposed over the shaft and is configured to dock onto the handle when not in use.

11 Claims, 18 Drawing Sheets

Related U.S. Application Data

(60) Provisional application No. 62/865,437, filed on Jun. 24, 2019.

(52) U.S. Cl.
CPC ....... *A61M 25/09* (2013.01); *A61M 2025/015* (2013.01); *A61M 2025/09008* (2013.01)

(56) References Cited

U.S. PATENT DOCUMENTS

| | | | |
|---|---|---|---|
| 5,364,352 A | 11/1994 | Cimino | |
| 5,466,230 A * | 11/1995 | Davila | A61M 25/0662 |
| | | | 604/528 |
| 5,573,520 A | 11/1996 | Schwartz | |
| 5,701,911 A * | 12/1997 | Sasamine | A61M 25/0905 |
| | | | 600/585 |
| 5,857,997 A | 1/1999 | Cimino | |
| 5,879,295 A | 3/1999 | Li | |
| 5,987,344 A | 11/1999 | West | |
| 6,132,390 A | 10/2000 | Cookston | |
| 6,179,809 B1 * | 1/2001 | Khairkhahan | A61M 25/0147 |
| | | | 604/95.04 |
| 6,287,280 B1 * | 9/2001 | Lampropoulos | A61M 39/0693 |
| | | | 604/167.03 |
| 6,394,976 B1 | 5/2002 | Winston | |
| 6,491,681 B1 * | 12/2002 | Kunis | A61M 25/0136 |
| | | | 604/528 |
| 6,554,794 B1 * | 4/2003 | Mueller | A61M 25/0141 |
| | | | 604/95.04 |
| 6,786,918 B1 * | 9/2004 | Krivoruchko | A61F 2/95 |
| | | | 606/198 |
| 6,793,667 B2 | 9/2004 | Herbert et al. | |
| 6,893,417 B2 * | 5/2005 | Gribbons | A61M 25/09041 |
| | | | 977/875 |
| 7,063,682 B1 * | 6/2006 | Whayne | A61B 18/1492 |
| | | | 606/41 |
| 7,101,361 B2 | 9/2006 | Gardeski | |
| 7,356,903 B2 * | 4/2008 | Krivoruchko | A61F 2/95 |
| | | | 29/451 |
| 7,604,660 B2 * | 10/2009 | Borg | A61B 90/30 |
| | | | 606/108 |
| 7,608,099 B2 * | 10/2009 | Johnson | A61F 2/95 |
| | | | 606/198 |
| 7,658,757 B2 * | 2/2010 | Moberg | A61F 2/95 |
| | | | 623/1.11 |
| 7,674,282 B2 * | 3/2010 | Wu | A61F 2/966 |
| | | | 623/1.11 |
| 8,808,345 B2 * | 8/2014 | Clark | A61B 34/74 |
| | | | 607/113 |
| 8,808,346 B2 * | 8/2014 | Jimenez, Jr. | A61F 2/95 |
| | | | 623/1.11 |
| 8,845,588 B2 * | 9/2014 | Bruszewski | A61M 39/0613 |
| | | | 604/167.03 |
| 9,149,607 B2 * | 10/2015 | Scheibe | A61M 25/0147 |
| 9,233,015 B2 * | 1/2016 | Geusen | A61F 2/95 |
| 9,445,928 B2 | 9/2016 | Argentine | |
| 9,656,042 B2 * | 5/2017 | Takagi | A61M 25/0097 |
| 10,369,031 B2 * | 8/2019 | Yang | A61F 2/9661 |
| 10,531,972 B2 | 1/2020 | Argentine | |
| 10,653,860 B2 | 5/2020 | Tang | |
| 11,083,362 B2 | 8/2021 | Schwarz | |
| 11,446,470 B2 * | 9/2022 | Castelli | A61F 2/9517 |
| 2003/0040735 A1 | 2/2003 | Kunis | |
| 2003/0109861 A1 | 6/2003 | Shimada | |
| 2005/0027306 A1 * | 2/2005 | Krivoruchko | A61F 2/95 |
| | | | 623/1.11 |
| 2005/0090890 A1 | 4/2005 | Wu | |
| 2005/0256452 A1 | 11/2005 | Demarchi | |
| 2006/0074477 A1 * | 4/2006 | Berthiaume | A61F 2/966 |
| | | | 623/1.11 |
| 2008/0065011 A1 * | 3/2008 | Marchand | A61F 2/2433 |
| | | | 604/103.05 |
| 2009/0018553 A1 | 1/2009 | McLean et al. | |
| 2009/0157162 A1 | 6/2009 | Chow | |
| 2010/0036472 A1 | 2/2010 | Papp | |
| 2010/0168756 A1 | 7/2010 | Dorn et al. | |
| 2010/0174290 A1 | 7/2010 | Wuebbeling et al. | |
| 2011/0144576 A1 | 6/2011 | Rothe | |
| 2011/0282425 A1 | 11/2011 | Dwork | |
| 2012/0053574 A1 | 3/2012 | Murray, III | |
| 2012/0158021 A1 | 6/2012 | Morrill | |
| 2012/0197303 A1 | 8/2012 | King et al. | |
| 2012/0289996 A1 | 11/2012 | Lee | |
| 2013/0012925 A1 * | 1/2013 | Berthiaume | A61M 25/0141 |
| | | | 604/528 |
| 2013/0253344 A1 | 9/2013 | Griswold | |
| 2014/0228800 A1 | 8/2014 | Rezac | |
| 2014/0324015 A1 | 10/2014 | Romoscanu | |
| 2016/0045311 A1 | 2/2016 | McCann et al. | |
| 2016/0374743 A1 * | 12/2016 | Beasley | A61B 18/04 |
| | | | 606/27 |
| 2018/0116843 A1 * | 5/2018 | Schreck | A61F 2/2418 |
| 2019/0351188 A1 | 11/2019 | Murphy | |
| 2020/0397574 A1 | 12/2020 | Marchand | |

FOREIGN PATENT DOCUMENTS

| | | |
|---|---|---|
| EP | 3673871 B1 | 12/2023 |
| WO | 2007139457 A1 | 12/2007 |
| WO | 2015143372 A2 | 9/2015 |
| WO | 2021030159 A1 | 2/2021 |

* cited by examiner

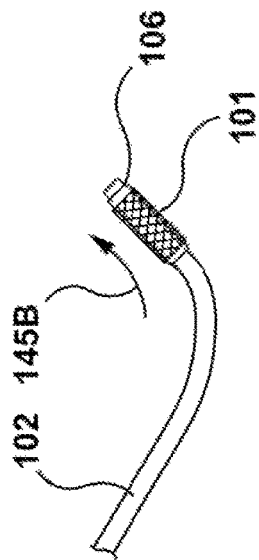
FIG. 1
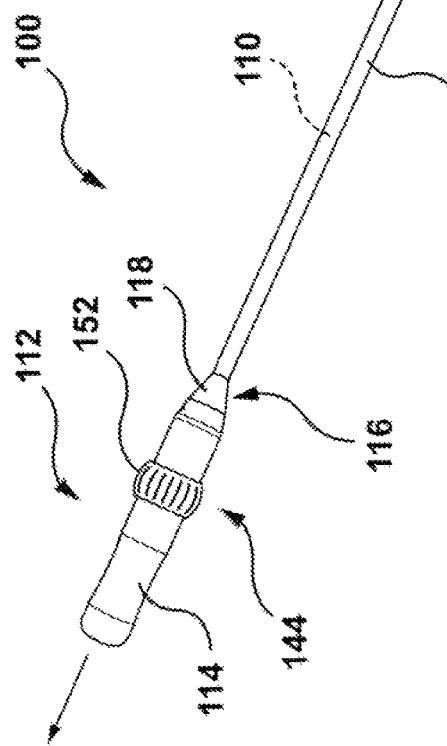
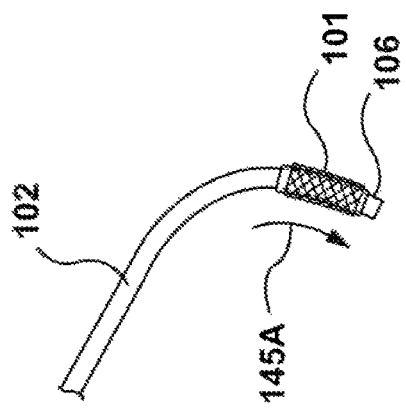
FIG. 2
FIG. 3

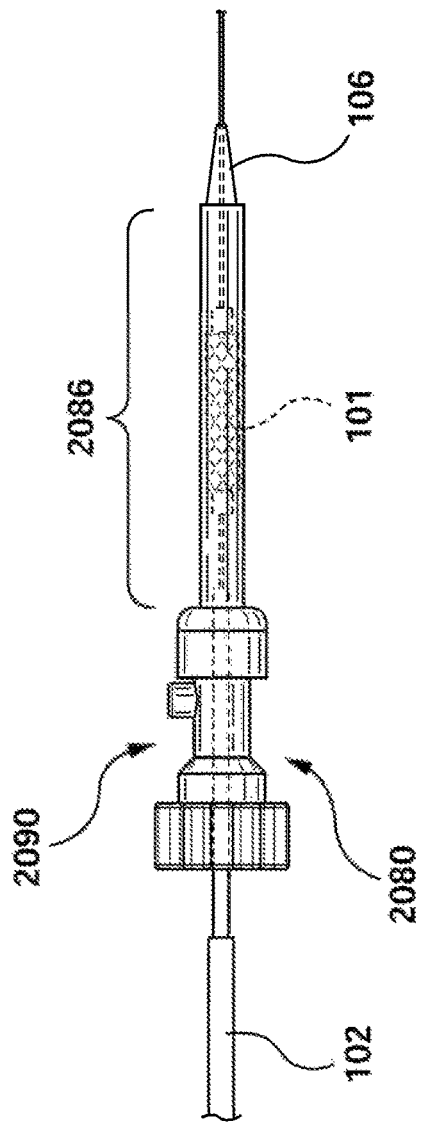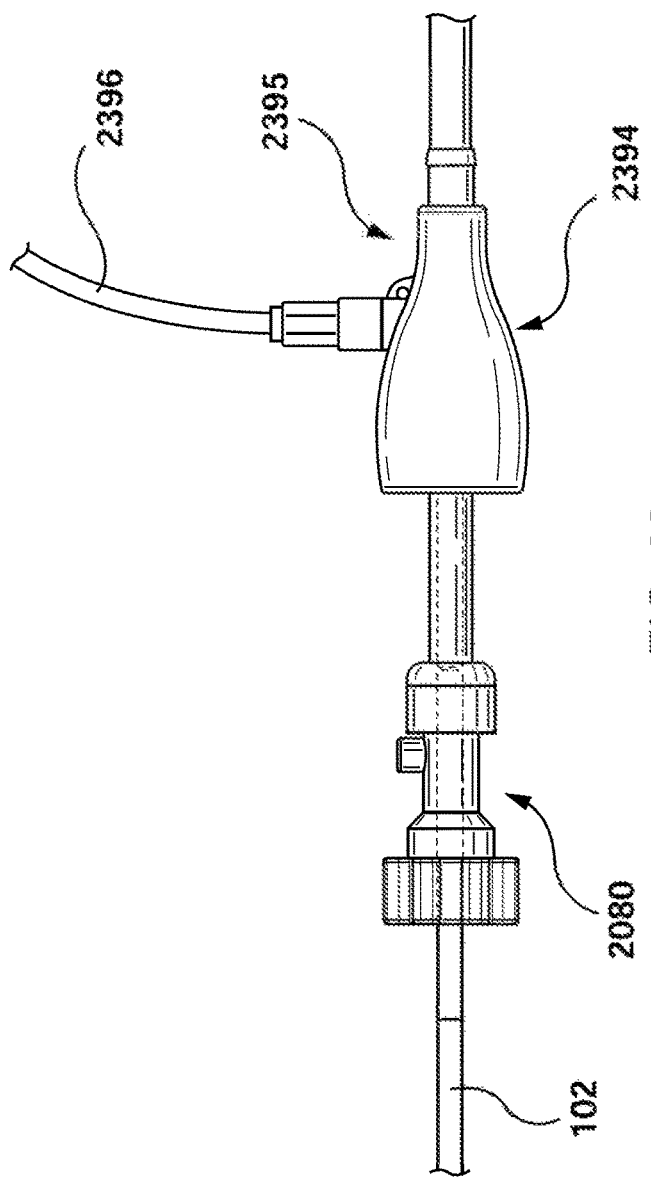

CATHETER HANDLE WITH TORQUE MECHANISM AND VALVE RELIEF COMPONENT

CROSS-REFERENCE TO RELATED APPLICATIONS

This application is a continuation of U.S. patent application Ser. No. 16/907,466, filed Jun. 22, 2020, which claims the benefit of U.S. Provisional Patent Application Ser. No. 62/865,437, filed Jun. 24, 2019, each of which is hereby incorporated by reference in its entirety for all purposes.

FIELD OF THE INVENTION

Embodiments hereof relate to catheters and more particularly to handles of a catheter or a delivery system.

BACKGROUND OF THE INVENTION

A variety of catheters for delivering a therapy and/or monitoring a physiological condition have been implanted or proposed for implantation in patients. Catheters may deliver therapy to, and/or monitor conditions associated with, the heart, muscle, nerve, brain, stomach or other organs or tissue. Many catheters are tracked through the vasculature to locate a therapeutic or diagnostic portion of the catheter at a target site. Such catheters must have flexibility to navigate the twists and turns of the vasculature, sufficient stiffness in the proximal portion thereof to be pushed through the vasculature alone or over a guidewire or through a lumen, and the capability of orienting a distal portion thereof in alignment with an anatomical feature at the target site so that a diagnostic or therapeutic procedure can be completed. In general terms, the catheter body must also resist kinking and be capable of being advanced through access pathways that twist and turn, sometimes abruptly at acute angles.

For certain procedures, it may be necessary for the clinician to accurately steer or deflect the catheter so that a distal opening thereof may be aligned with an ostium of a branch or side vessel. The distal portions of catheters frequently need to be selectively curved or bent and straightened again while being advanced within the patient to steer the catheter distal end into a desired body lumen or chamber. For example, it may be necessary to direct the catheter distal end through tortuous anatomies and/or into a branch at a vessel bifurcation. In addition, some procedures require high accuracy in guidewire orientation. For example, often patient's arteries are irregularly shaped, highly tortuous and very narrow. The tortuous configuration of the arteries may present difficulties to a clinician in advancement of a catheter to a treatment site.

In addition to bending or deflecting the distal portion of the catheter during navigation, the clinician may also need to rotate or torque the catheter when advancing the catheter to a treatment site in order to achieve proper or desired alignment of the catheter. Currently, clinicians grasp and rotate the entire handle of the catheter in order to manually torque the catheter. However, manually torqueing the entire device causes unstable movement of the catheter while inside the patient and may require significant force to combat recoiling forces. Additionally, when the handle of the catheter is rotated during torqueing, the controls on the handle may be placed in a position that limit the ability to use them.

Thus, a need in the art still generally exists for improved apparatuses and methods for navigating a catheter through or within a patient's anatomy.

BRIEF SUMMARY OF THE INVENTION

Embodiments hereof are related to a catheter including a handle and a shaft extending from within the handle, wherein the handle includes a housing and a torqueing mechanism disposed at least partially within an interior of the housing of the handle. The torqueing mechanism includes a nosecone rotatable relative to the housing of the handle and a bearing coupled to the nosecone to be rotatable therewith. The bearing is concentrically disposed over the shaft and is configured to transmit a torque from the nosecone to the shaft when the nosecone is rotated such that rotation of the nosecone causes an entire length of the shaft to rotate therewith.

Embodiments hereof also relate to a catheter including a handle and a shaft extending from within the handle, wherein the handle includes a housing, a torqueing mechanism disposed at least partially within an interior of the housing of the handle, and a steering mechanism disposed at least partially within the interior of the housing of the handle. The torqueing mechanism includes a nosecone rotatable relative to the housing of the handle and a bearing coupled to the nosecone to be rotatable therewith. The bearing is concentrically disposed over the shaft and is configured to transmit a torque from the nosecone to the shaft when the nosecone is rotated. The steering mechanism includes a rack and a pull wire having a proximal end attached to the bearing and a distal end attached to a distal portion of the shaft. The rack is coupled to the bearing such that the bearing is slideable therewith. Rotation of the nosecone causes an entire length of the shaft to rotate therewith and the bearing rotates relative to the rack during rotation thereof, and axial movement of the rack tensions the pull wire to bend the distal portion of the shaft and the bearing slides relative to the shaft and relative to the nosecone during axial movement thereof.

Embodiments hereof also relate to a catheter including a handle and a shaft extending from within the handle, wherein the handle includes a housing, a nosecone rotatable relative to the housing of the handle, a bearing concentrically disposed over the shaft and configured to transmit a torque to the shaft when the bearing is rotated, a rack, and a pull wire having a proximal end attached to the bearing and a distal end attached to a distal portion of the shaft. The bearing is coupled to the nosecone to be rotatable therewith, and the rack is coupled to the bearing such that the bearing is slideable therewith. Rotation of the nosecone causes an entire length of the shaft to rotate therewith and the bearing rotates relative to the rack during rotation thereof, and axial movement of the rack tensions the pull wire to bend the distal portion of the shaft and the bearing slides relative to the shaft and relative to the nosecone during axial movement thereof.

Embodiments hereof also relate to a catheter including a handle, a shaft distally extending from the handle, a strain relief component concentrically disposed over a portion of the shaft and distally extending from the handle, a balloon-expandable prosthesis disposed on a distal portion of the shaft, and a valve relief component slidingly disposed over an outer surface of the shaft. The valve relief component is configured to be selectively disposed over the balloon-expandable prosthesis to protect the balloon-expandable prosthesis during insertion into an introducer sheath. The strain relief component is configured to serve as a docking station for the valve relief component when the strain relief component is not disposed over the balloon-expandable prosthesis.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a side view of a catheter or delivery system according to an embodiment hereof, wherein the catheter includes a handle including both a torqueing mechanism and a steering mechanism and wherein the catheter includes a balloon-expandable prosthesis disposed at a distal portion thereof.

FIG. 2 is a side view of the distal portion of the catheter of FIG. 1, wherein the distal portion is bent in a first direction via the steering mechanism of the handle of the catheter.

FIG. 3 is a side view of the distal portion of the catheter of FIG. 1, wherein the distal portion is bent in a second or opposing direction via the steering mechanism of the handle of the catheter.

FIG. 22 is a side view of the distal portion of the catheter of FIG. 1, wherein the valve relief component of FIG. 20 is disposed over the balloon-expandable prosthesis.

FIG. 23 is a side view of the distal portion of the catheter of FIG. 1, wherein the catheter is being inserted through an introducer sheath with the valve relief component of FIG. 20 disposed over the balloon-expandable prosthesis.

DETAILED DESCRIPTION OF THE INVENTION

Figure 4:
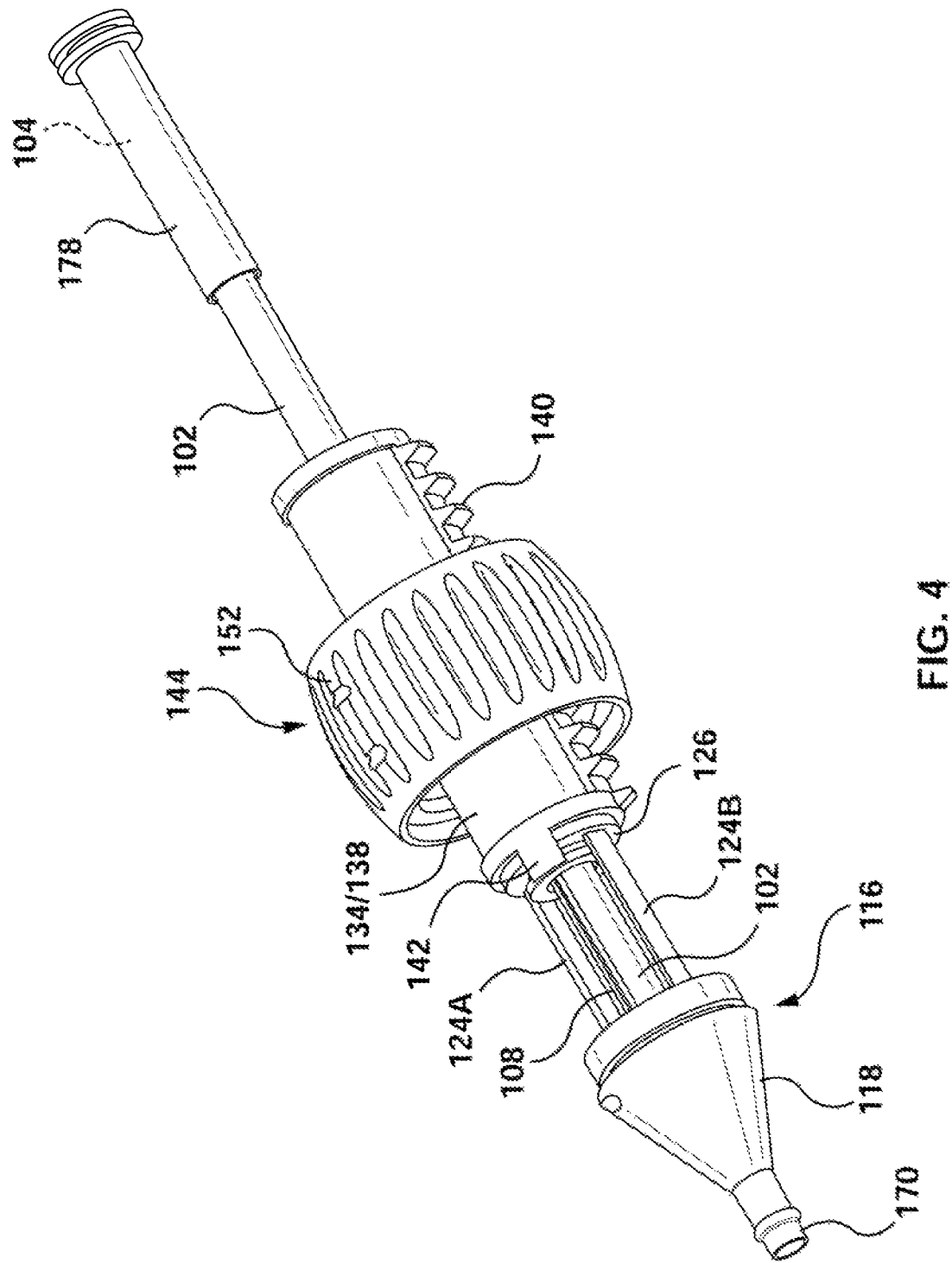
FIG. 4 is a perspective view of the handle of the catheter of FIG. 1, wherein a shell or housing of the handle is removed for illustrative purposes.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. In addition, "slidably" or "slidable" denotes back and forth movement in a longitudinal direction about a longitudinal axis LA of the handle (shown in FIG. 1) while "rotatably" or "rotatable" denotes movement or rotation about the longitudinal axis LA of the handle.

The following detailed description is merely exemplary in nature and is not intended to limit the invention or the application and uses of the invention. Although the description of the invention is in the context of delivery of a balloon-expandable prosthesis, the invention may also be used where it is deemed useful in endoscopic procedures, procedures in the coronary vessels, or procedures in the peripheral vessels. Furthermore, there is no intention to be bound by any expressed or implied theory presented in the preceding technical field, background, brief summary or the following detailed description.

Embodiments hereof relate to a handle for a delivery catheter or other catheter device, the handle including a torqueing mechanism. The torqueing mechanism includes a nosecone rotatable relative to the housing of the handle and a bearing coupled to the nosecone to be rotatable therewith. The bearing is concentrically disposed over a shaft of the catheter and is configured to transmit a torque from the nosecone to the shaft when the nosecone is rotated. Rotation of the nosecone causes an entire length of the shaft to rotate therewith. The handle thus has the capability of torqueing the entire length of the shaft with an actuator (i.e., the rotatable nosecone), circumferentially to an exact degree, allowing for increased stability of the handle during use. Stated another way, the handle itself does not need to be twisted or rotated in order to direct the distal tip of the shaft and thus other controls or actuators on the handle remain stationary and accessible to the user during the procedure. The handle also includes a steering mechanism to apply tension on a pull wire to bend a distal portion of the shaft, with both the torqueing and steering mechanisms integrated into the handle such that operation of the torqueing mechanism does not interfere with operation of the steering mechanism. In addition, the catheter further includes a valve relief component that serves also to relieve strain of the distal portion of the catheter when the catheter is inserted through an introducer sheath. The valve relief component may be secured onto the handle after insertion through the introducer sheath to ensure it does not slide on the catheter during the procedure.

The catheter will now be described in more detail with reference to the figures. With reference to FIG. 1, a catheter 100 includes a handle 112 and a shaft 102 having a distal end 106 opposite the handle 112. The handle 112 includes both a torqueing mechanism 116 and a steering mechanism 144 as will be described in greater detail herein. Shaft 102 defines a central lumen 110 such that catheter 100 may be slidingly disposed and track over a guidewire (not shown). Shaft 102 may further define additional lumens depending upon the particular configuration of the catheter 100. A balloon-expandable prosthesis 101 is mounted over a balloon 105 disposed on a distal portion of the shaft 102. The balloon-expandable prosthesis 101 is shown in its delivery or unexpanded configuration in FIG. 1, but it will be understood by those of ordinary skill in the art that after deployment, the balloon-expandable prosthesis 101 is radially expanded or deployed by the balloon 105 and released from the catheter 100 at a desired location in a patient's body lumen. The configuration of the balloon-expandable prosthesis 101 is merely exemplary, and it would be apparent to one of ordinary skill in the art that catheter 100 may be utilized for delivering and deploying various types or configurations of prostheses. Further, although depicted as a delivery catheter for the balloon-expandable prosthesis 101, the catheter 100 is not required to be configured for delivering a prosthesis but rather the catheter 100 having the handle 112 may be utilized in other procedures or for other purposes including diagnostic purposes. The handle 112 having both the torqueing mechanism 116 and the steering mechanism 144 is advantageous in any type of catheter that may require torqueing and/or steering during navigation in situ. Although the catheter 100 described herein is a stand-alone delivery catheter for delivering the balloon-expandable prosthesis 101, in another embodiment hereof (not shown), the catheter 100 forms an outer component of another type of treatment or delivery system.

The torqueing mechanism 116 permits the distal portion of the catheter 100 to be rotated as indicated by the directional arrow 117 by turning a nosecone 118 disposed at the distal end of the handle 112 while holding the proximal end of the handle 112 which contains the remaining controls. The steering mechanism 144 includes a pull wire 146 (shown on FIGS. 18 and 19) which is attached to the distal end 106 of the shaft 102 to be selectively tensioned in order to bend the distal end 106 of the catheter. The pull wire 146 is configured to rotate to the same degree as the shaft 102 when the catheter 100 is being torqued via rotation of the nosecone 118. When the pull wire 146 is retracted via the steering mechanism 144, the pull wire 146 is placed under tension to bend or deflect the distal portion of the catheter 100. For example, FIG. 2 is a side view of the distal portion of the catheter 100 that illustrates the distal portion of the catheter 100 bent in a first direction via the steering mechanism 144 as illustrated by directional arrow 145A. If it is desired to bend or deflect the distal portion of the catheter 100 in an opposing direction (i.e., a second direction opposite from the first direction as illustrated by directional arrow 145B in FIG. 3), the torqueing mechanism 116 may be actuated to rotate the catheter approximately 180 degrees and then the steering mechanism 144 may be actuated to bend the distal portion of the catheter 100.

Figure 5:
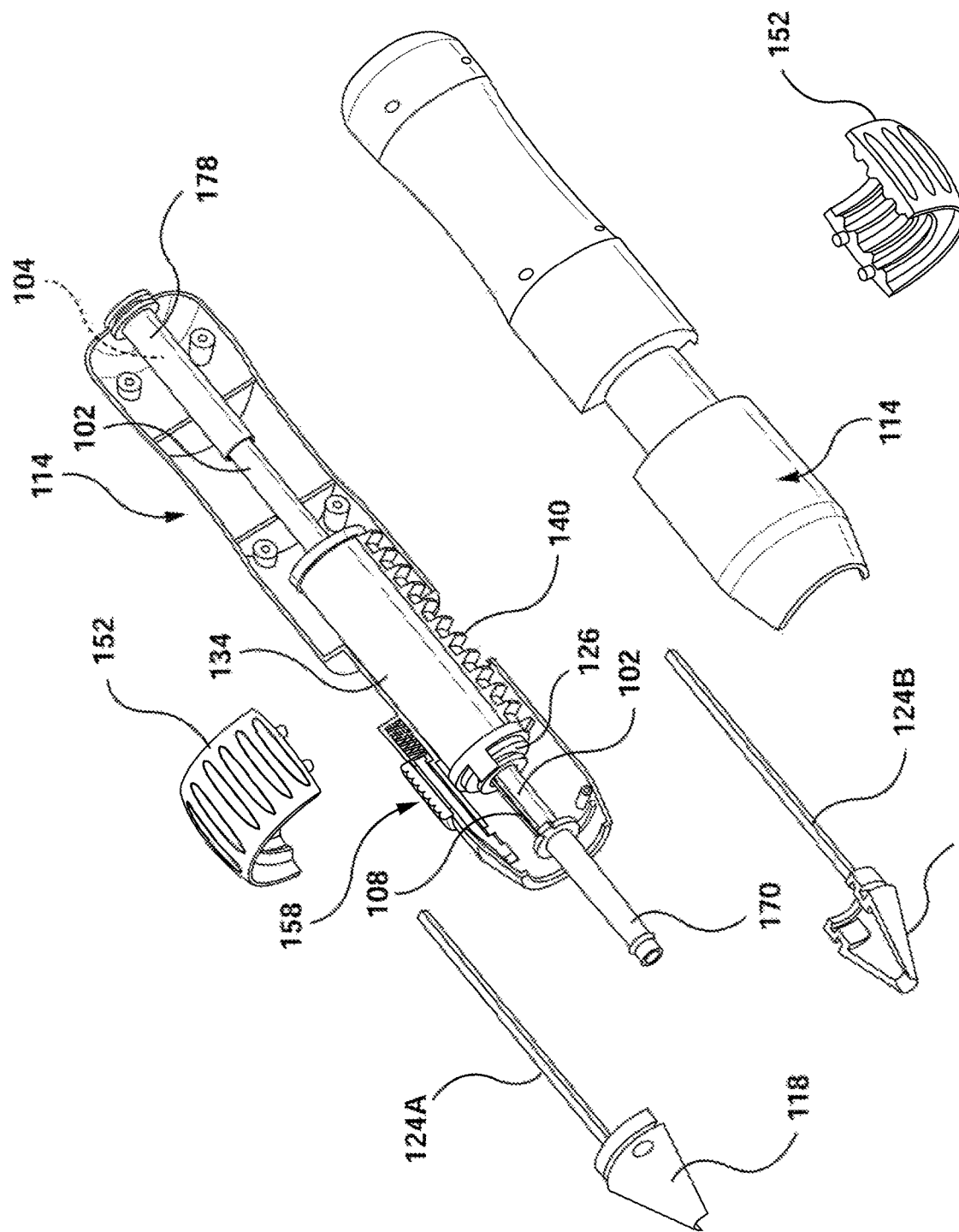
FIG. 5 is an exploded perspective view of the handle of the catheter of FIG. 1.

The handle 112 includes a housing or shell 114 which houses the internal components of the handle 112. The components of the handle 112 will now be introduced with reference to FIGS. 4 and 5, with FIG. 4 being a perspective view of the handle 112 with the housing 114 thereof removed for illustrative purposes and FIG. 5 being an exploded perspective view of the handle 112. In addition to the housing 114, the handle 112 includes the nosecone 118 which is rotatable relative to the housing 114, a bearing 126 which is disposed within the housing 114 and is concentrically disposed over the shaft 102, a rack 134 coupled to the bearing 126, the pull wire 146 (shown on FIGS. 18 and 19), a locking mechanism 158, a strain relief component 170 disposed over a portion of the shaft 102 at a distal end of the housing 114, and a luer fitting 178 disposed over a portion of the shaft 102 at a proximal end of the housing 114. The luer fitting 178 is attached to the housing 114 and the shaft 102 is disposed through the luer fitting 178 such that the shaft 102 is configured to freely rotate or spin within the luer fitting 178 and thus be rotatable relative to the housing 114.

Figure 6:
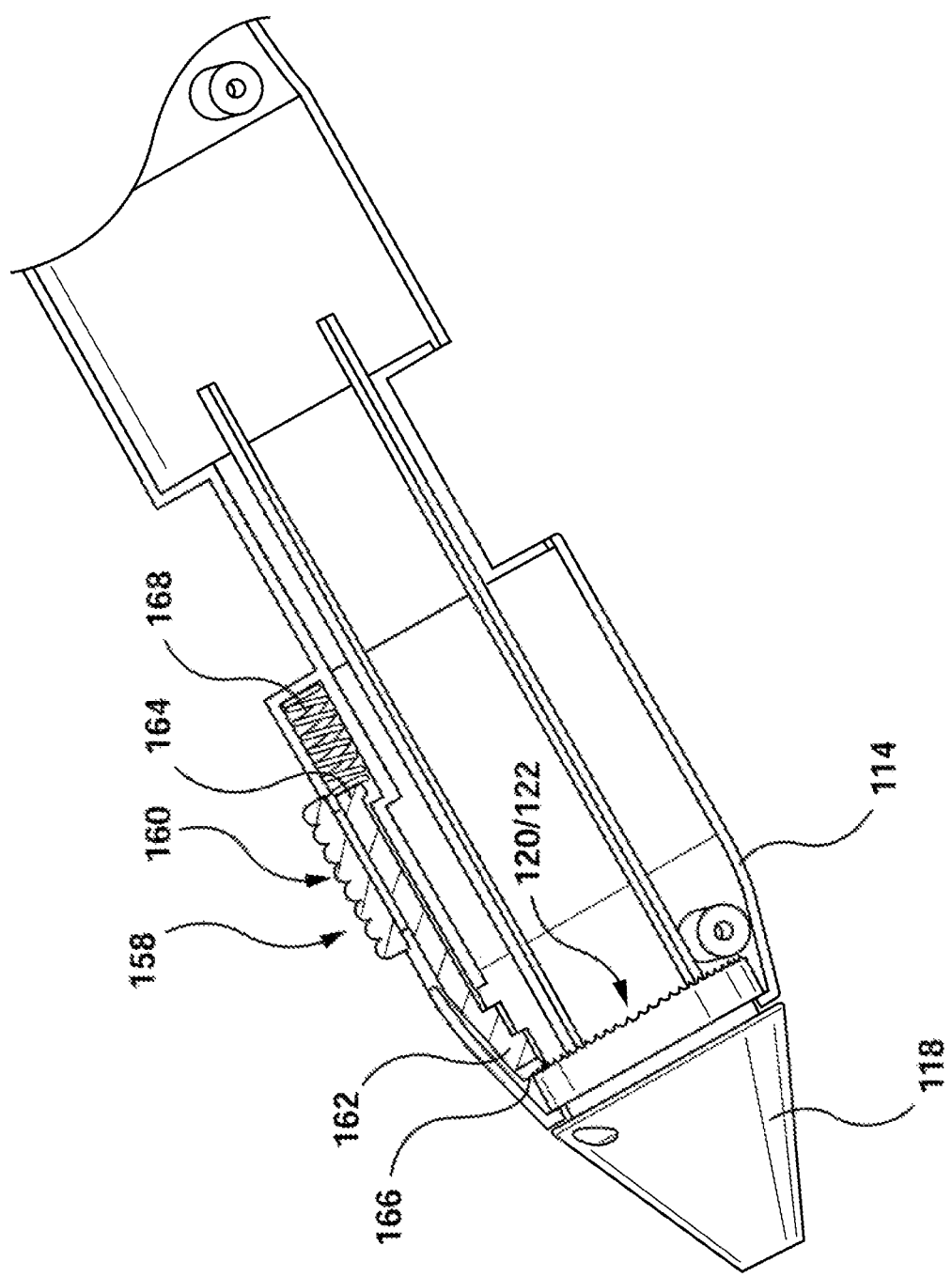
FIG. 6 is a side view of a distal portion of the handle of the catheter of FIG. 1, wherein a portion of the housing, a nosecone, and a locking mechanism of the handle are shown with the remaining components removed for illustrative purposes.
Figure 7:
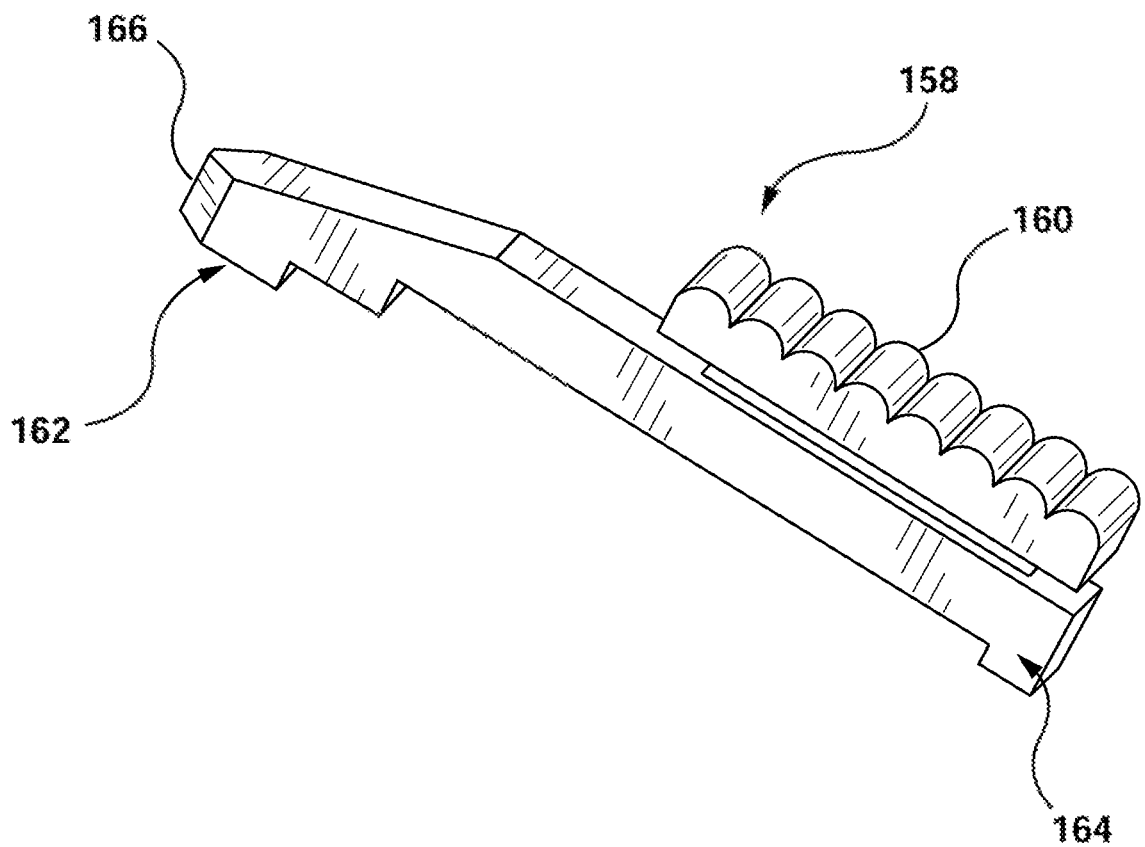
FIG. 7 is a perspective view of a slider of the locking mechanism of the handle of the catheter of FIG. 1, wherein the slider is removed from the handle for illustrative purposes.

With additional reference to FIGS. 6 and 7, the locking mechanism 158 is configured to lock a circumferential position of the nosecone 118 relative to the housing 114 of the handle 112. FIG. 6 is a side view of a distal portion of the handle 112, wherein a portion of the housing 114, the nosecone 118, and the locking mechanism 158 are shown with the remaining components removed for illustrative purposes. FIG. 7 is a perspective view of a slider 160 of the locking mechanism 158 removed from the handle 112 for illustrative purposes. The locking mechanism 158 includes the slider 160 accessible and operable from an exterior of the housing 114 of the handle 112 and a spring 168 disposed within a recess within the housing 114. A proximal end 164 of the slider 160 abuts against and contacts the spring 168. The slider 160 has a tooth or pointed tip 166 formed at a distal end 162 thereof that is configured to selectively engage or mate with a plurality of teeth 122 formed on a proximal end surface 120 of the nosecone 118. When the pointed tip 166 of the slider 160 engages or mates with one of the plurality of teeth 122 of the nosecone 118, the nosecone 118 is in a locked configuration and cannot be rotated or spun by the user. Stated another way, the pointed tip of the slider 160 fits into one of the plurality of teeth 122 of the nosecone 118 to hold the nosecone 118 in the locked configuration. As such, the slider 160 locks a circumferential position of the nosecone 118 relative to the housing 114 of the handle 112. A user is thus prevented from inadvertently spinning or rotating the nosecone 118 when the nosecone 118 is in the locked configuration.

When it is desired to torque the shaft 102 of the catheter 100, the slider 160 is proximally retracted such that the pointed tip 166 of the slider 160 is withdrawn from the teeth 122 of the nosecone 118, thereby releasing the nosecone 118 to be in an unlocked configuration. When retracted in a proximal direction, the slider 160 compresses the spring 168 and is permitted to move in a proximal direction to disengage from the nosecone 118. When in the unlocked configuration, the nosecone 118 may be rotated in order to torque the catheter 100. Once the catheter 100 is torqued as desired, the user may release the slider 158 such that the spring 168 resumes its uncompressed configuration, thereby distally advancing the slider 158 to re-engage with the nosecone 118 such that the pointed tip 166 of the slider 160 is positioned within one of the plurality of teeth 122 of the nosecone 118. Stated another way, when the slider 160 is released, the tension within the spring 168 and the sufficient resiliency of the spring 168 causes the slider 160 to move distally and contact the proximal end surface 120 of the nosecone 118, thereby securing the nosecone 118 in its locked configuration.

Figure 8A:
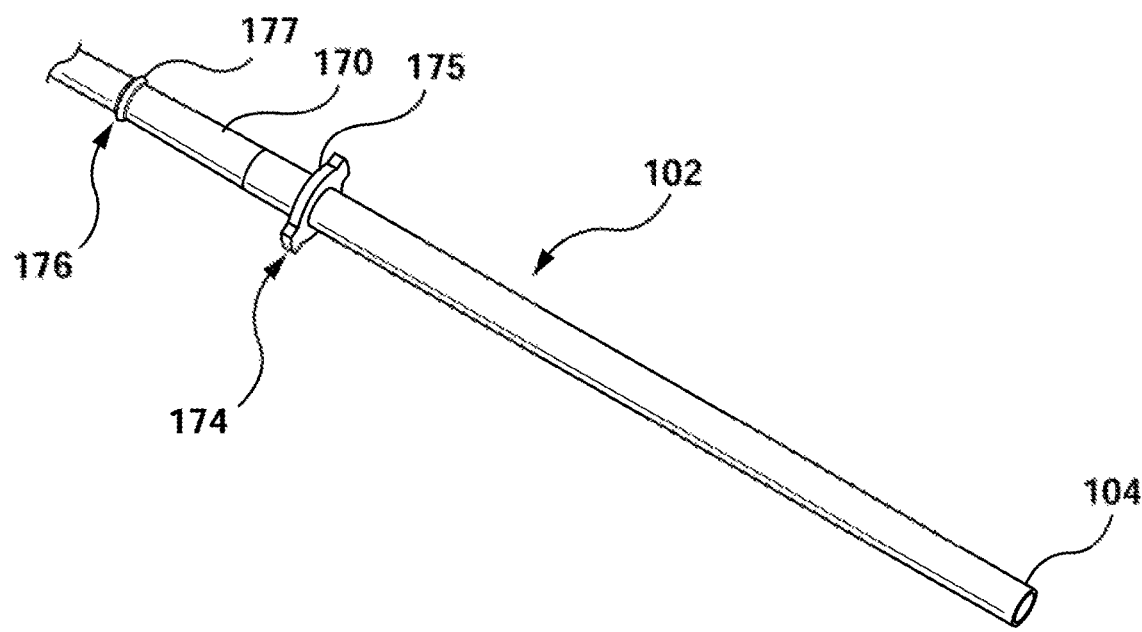
FIG. 8A is a perspective view of a portion of a shaft of the catheter of FIG. 1 and a strain relief segment disposed over the shaft, wherein the shaft and the strain relief segment are removed from the catheter for illustrative purposes.
Figure 8B:
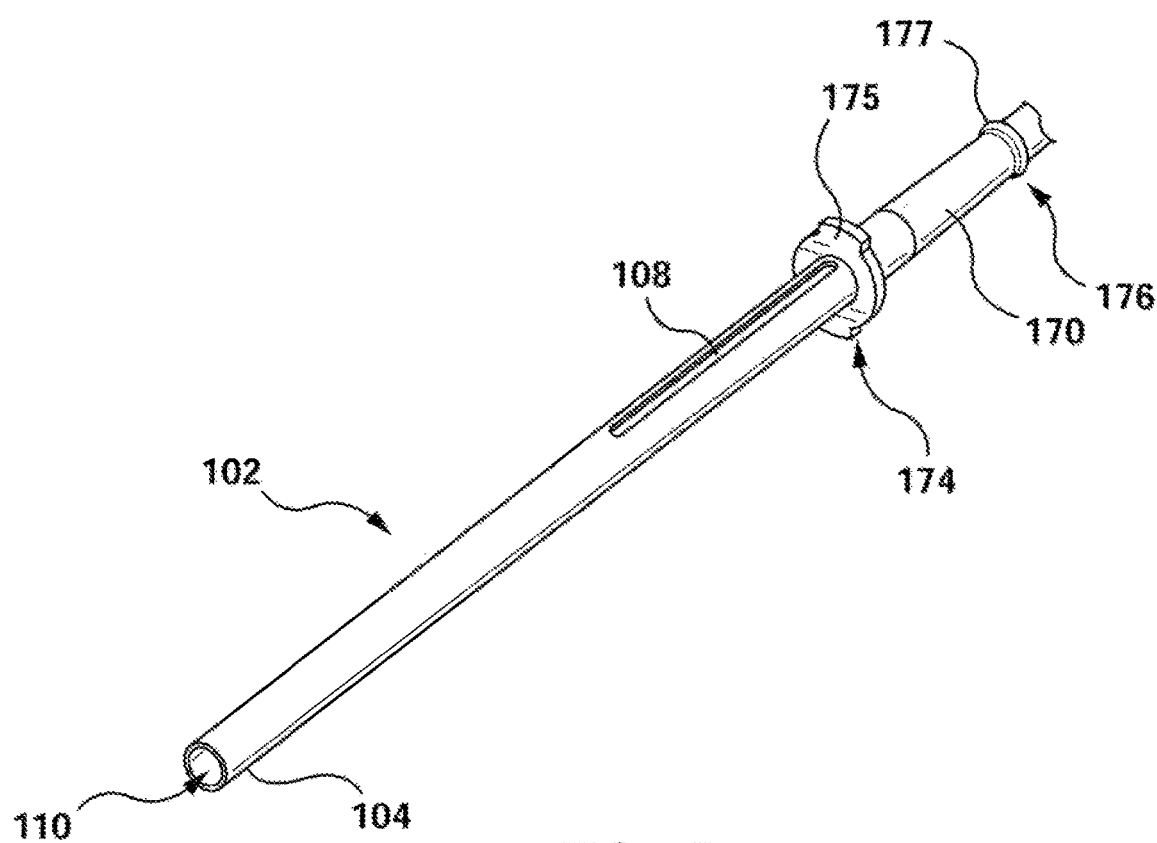
FIG. 8B is another perspective view of the portion of the shaft of the catheter of FIG. 1 and the strain relief segment disposed over the shaft, wherein the shaft and the strain relief segment are removed from the catheter for illustrative purposes.

FIGS. 8A and 8B are perspective views of a portion of the shaft 102 and the strain relief component 170 removed from the catheter 100 for illustrative purposes. The shaft 102 is an elongate tubular or cylindrical element defining the central lumen 110 that extends from a proximal end 104 to the distal end 106 thereof. The central lumen 110 is open at the distal end 106 of the shaft 102 which in turn forms the distal end of the catheter 100. In an embodiment hereof, the central lumen 110 is sized or configured to slidingly receive a guidewire there-through. The shaft 102 includes an elongated slot or channel 108 formed through a sidewall thereof. The elongated slot 108 is disposed within the handle 112, distal to the bearing 126, and functions to permit the pull wire 146 to exit from within the central lumen 110 as will be described in more detail herein with respect to FIGS. 18 and 19. In an embodiment, the shaft 102 may be sized to be used with an introducer sheath with the central lumen 110 being sized to accommodate a guidewire having an outer diameter of 0.035 inch. The proximal end 104 of the shaft 102 extends out of the patient and is disposed within the handle 112.

The shaft 102 also includes an inflation lumen (not shown) to allow inflation fluid to be delivered to the balloon. In an embodiment, the inflation lumen is preformed in a sidewall of the shaft 102 and may be formed for example by multi-lumen profile extrusion. The inflation lumen extends adjacent or parallel to the central lumen 110 but terminates at the balloon 105, proximal to the distal end 106 of the shaft 102. The inflation lumen is in fluid communication with an interior of the balloon 105 to permit inflation fluid to be delivered to the interior of the balloon 105 and radially expand the balloon 105 when desired. In another embodiment, the inflation lumen may alternatively be formed via an annular space formed between an inner shaft component concentrically disposed within the shaft 102, or via an elongated inflation tube disposed within and attached to the shaft 102, as will be understood by those of ordinary skill in the art of balloon catheter construction. It would also be understood by one of ordinary skill in the art of balloon catheter design that the luer fitting 178, or some other type of fitting, may be connected to a source of inflation fluid (not shown) and may be of another construction or configuration without departing from the scope of the present invention.

The shaft 102 may be formed of one or more polymeric materials, non-exhaustive examples of which include polyethylene, polyethylene block amide copolymer (PEBA), polyamide and/or combinations thereof, either laminated, blended or co-extruded. Optionally, the shaft 102 or some portion thereof may be formed as a composite having a reinforcement layer incorporated within a polymeric body in order to enhance strength and/or flexibility. Suitable reinforcement layers include braiding, wire mesh layers, embedded axial wires, embedded helical or circumferential wires, hypotubes, and the like. In one embodiment, for example, at least a proximal portion of the shaft 102 may be formed from a reinforced polymeric tube. In accordance with embodiments hereof, the balloon 105 may be formed of any suitable polymeric material used for dilatation balloon manufacturing, for instance, polyether block amide (PEBA) and polyurethane (PU), and may have an outer diameter in the range of 2-4 mm and a length in the range of 5-15 mm.

The strain relief component 170 is concentrically disposed over a portion of the shaft 102 at a distal end of the housing 114 and functions to relieve stress from the shaft 102 as it exits from the distal end of the housing 114. The strain relief component 170 is a relatively short tubular component that defines a lumen therethrough that extends from a proximal end 174 to a distal end 176 thereof. The proximal end 174 includes a radial flange 175 that is attached to the interior of the nosecone 118. The distal end 176 of the strain relief component 170 extends or protrudes from a distal end of the housing 114 of the handle 112 and includes a circumferential bump or raised ring 177 that is configured to mate with a valve relief component as will be described in more detail herein with respect to FIGS. 20-30. As will be described in more detail herein, the valve relief component is a component that is slidingly disposed over an outer surface on the shaft 102 and is configured to be selectively disposed over the balloon-expandable prosthesis 101 to protect the balloon-expandable prosthesis 101 during insertion into an introducer sheath. The strain relief component 170 is configured to serve as a docking station for the valve relief component when the valve relief component is not disposed over the balloon-expandable prosthesis 101. The valve relief component is secured or docked onto the raised ring 177 of the strain relief component 170 through an interference fit.

The torqueing mechanism 116 of the handle 112 will now be described in more detail. The torqueing mechanism 116 includes the nosecone 118 and the bearing 126, which are rotatably coupled together such that rotation of the nosecone 118 also results in rotation of the bearing 126. The bearing 126 is also rotatably coupled to the shaft 102 such that rotation of the bearing 126, which is concentrically disposed over the shaft 102, further results in rotation of the shaft 102. Thus, the torqueing mechanism 116 permits the distal portion of the catheter 100 to be rotated by turning a nosecone 118 of the handle 112.

Figure 9A:
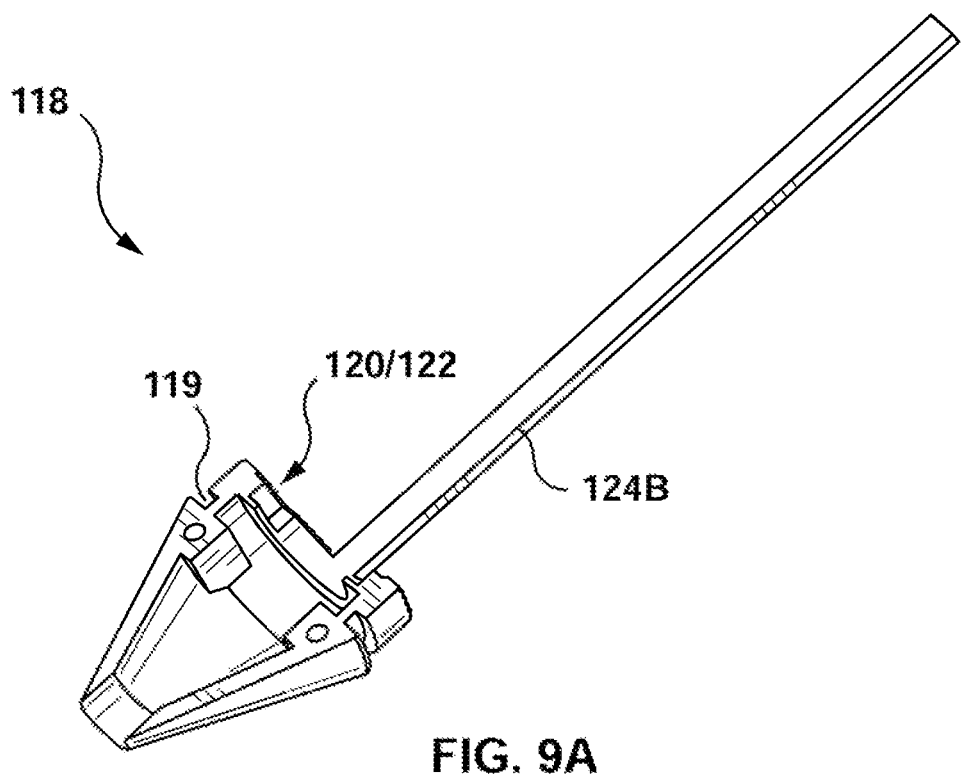
FIG. 9A is a perspective view of a portion of the nosecone of the handle of the catheter of FIG. 1, wherein the nosecone is removed from the handle for illustrative purposes.
Figure 9B:
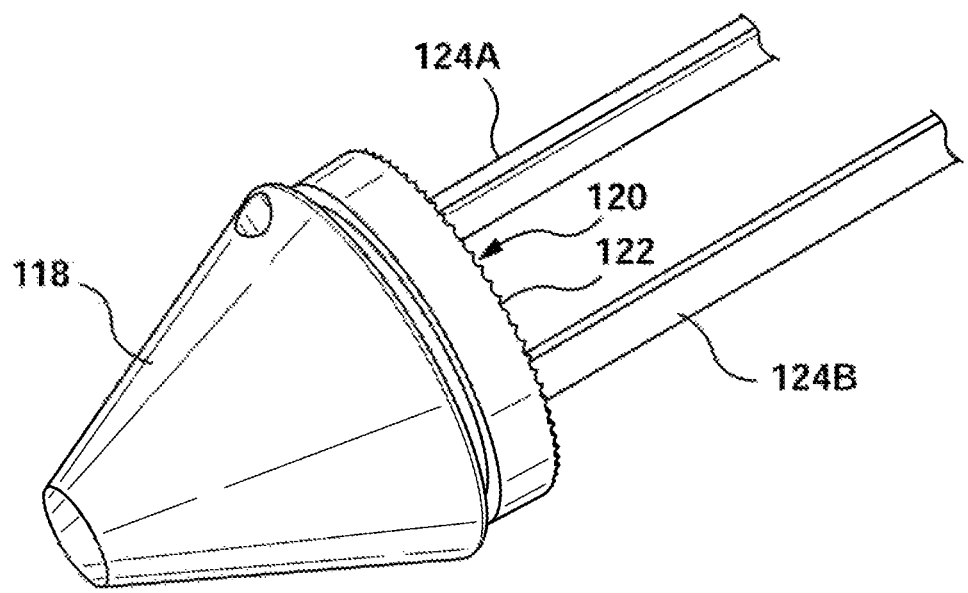
FIG. 9B is a perspective view of a distal portion of the nosecone of the handle of the catheter of FIG. 1, wherein the nosecone is removed from the handle for illustrative purposes.
Figure 11:
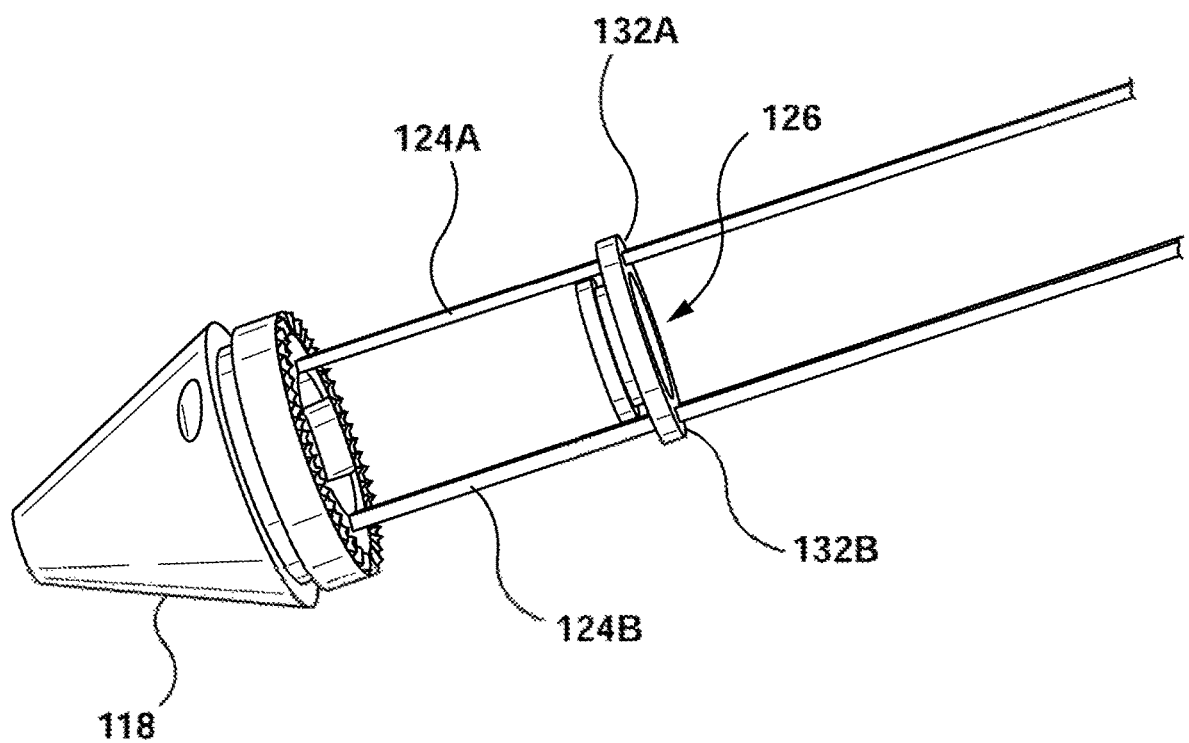
FIG. 11 is a perspective view of an assembly of the nosecone and the bearing of the handle of the catheter of FIG. 1, wherein the assembly is removed from the handle for illustrative purposes.

More particularly, FIGS. 9A and 9B illustrate the nosecone 118 removed from the handle 112 for illustrative purposes only. FIG. 9A is a perspective sectional view of the nosecone 118 and FIG. 9B is a perspective view of a distal portion of the nosecone 118. The nosecone 118 is accessible and operable from an exterior of the housing 114. The nosecone 118 has a truncated hollow conical configuration such that the shaft 102 extends therethrough. The proximal end surface 120 of the nosecone 118 includes the plurality of teeth 122 that interact with the locking mechanism 158 as described above with respect to FIGS. 6 and 7. The nosecone 118 also includes a circumferential groove 119 formed on an outer surface thereof for coupling the nosecone 118 to a distal end of the housing 114. The nosecone 118 further includes first and second fingers 124A, 124B proximally extending from the proximal end surface 120 of the nosecone 118. The first and second fingers 124A, 124B are disposed at circumferentially opposing locations of the nosecone 118, and serve to couple the nosecone 118 to the bearing 126 as best shown in FIG. 11 which is an assembly of the nosecone 118 and the bearing 126.

Figure 10:
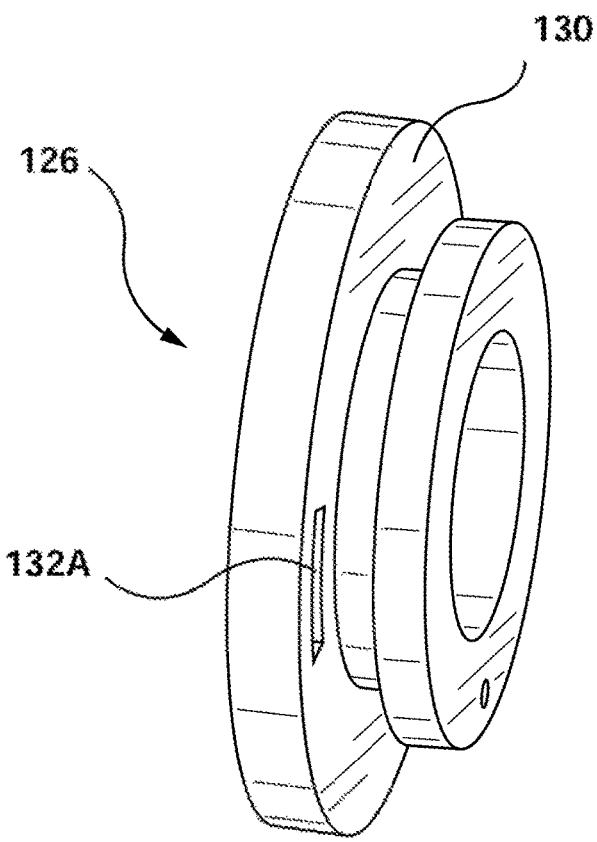
FIG. 10 is a perspective view of a bearing of the handle of the catheter of FIG. 1, wherein the bearing is removed from the handle for illustrative purposes.
Figure 10A:
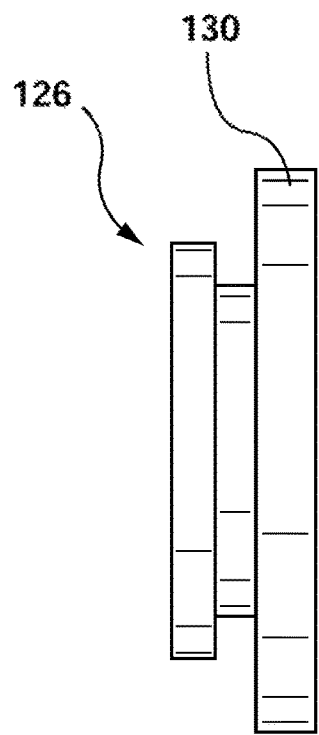
FIG. 10A is a side view of the bearing of the handle of the catheter of FIG. 1, wherein the bearing is removed from the handle for illustrative purposes.
Figure 10B:
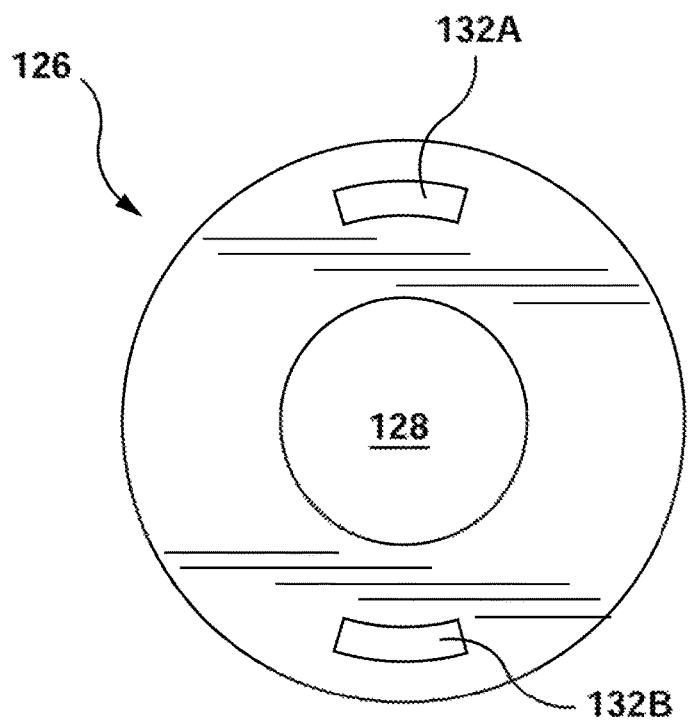
FIG. 10B is a front view of the bearing of the handle of the catheter of FIG. 1, wherein the bearing is removed from the handle for illustrative purposes.

FIGS. 10, 10A, and 10B illustrate the bearing 126 removed from the handle 112 for illustrative purposes only. FIG. 10 is a perspective view of the bearing 126, which FIG. 10A is a side view and FIG. 10B is a front view. The bearing 126 is disposed within the interior of the housing 114 of the handle 112. The bearing 126 is a tubular component that defines a lumen 128 therethough. The bearing 126 is concentrically disposed over the shaft 112 such that the shaft 112 extends through the lumen 128. The bearing 126 also includes a radial flange 130 at a proximal end thereof. The radial flange 130 includes first and second slots 132A, 132B formed therethrough. The first and second slots 132A, 132B are sized and configured to receive the first and second fingers 124A, 124B, respectively, of the nosecone 118. The first and second fingers 124A, 124B will extend through and be secured within the first and second slots 132A, 132B, respectively, through an interference fit as best shown in FIG. 11 which is an assembly of the nosecone 118 and the bearing 126. Via the first and second fingers 124A, 124B, the bearing 126 is coupled to the nosecone 118 to be rotatable therewith.

The bearing 126 is configured to transmit a torque or a drive to the shaft 102 when the bearing 126 is rotated. In an embodiment, the bearing 126 is a roller-type bearing in which torque is positively transmitted by rollers (not shown) that wedge against interior ramps or may be another type of uni-directional bearing known in the art. The bearing 126 transmits a torque from the nosecone 118 to the shaft 102 when the nosecone 118 is rotated in either direction, i.e., counter-clockwise or clockwise. Thus, when the nosecone 118 is rotated by a user, the bearing 126 and the shaft 102 rotate with the nosecone 118. Rotation of the nosecone 118 causes an entire length of the shaft 102 to rotate therewith, and thus the torqueing mechanism 116 may be utilized to torque the distal portion of the catheter 100.

The steering mechanism 144 of the handle 112 will now be described in more detail. The steering mechanism 144 includes a knob 152 which is rotatable relative to the housing 114 of the handle 112, the rack 134 concentrically disposed within the knob 152 and coupled to the bearing 126, and the pull wire 146 (shown and described with respect to FIGS. 18 and 19 below). The pull wire 146 is attached to the distal end 106 of the shaft 102 to be selectively tensioned in order to bend the distal end 106 of the catheter. Stated another way, when the pull wire 146 is retracted via the steering mechanism 144, the pull wire 146 is placed under tension and bends the distal portion of the catheter 100.

Figure 12:
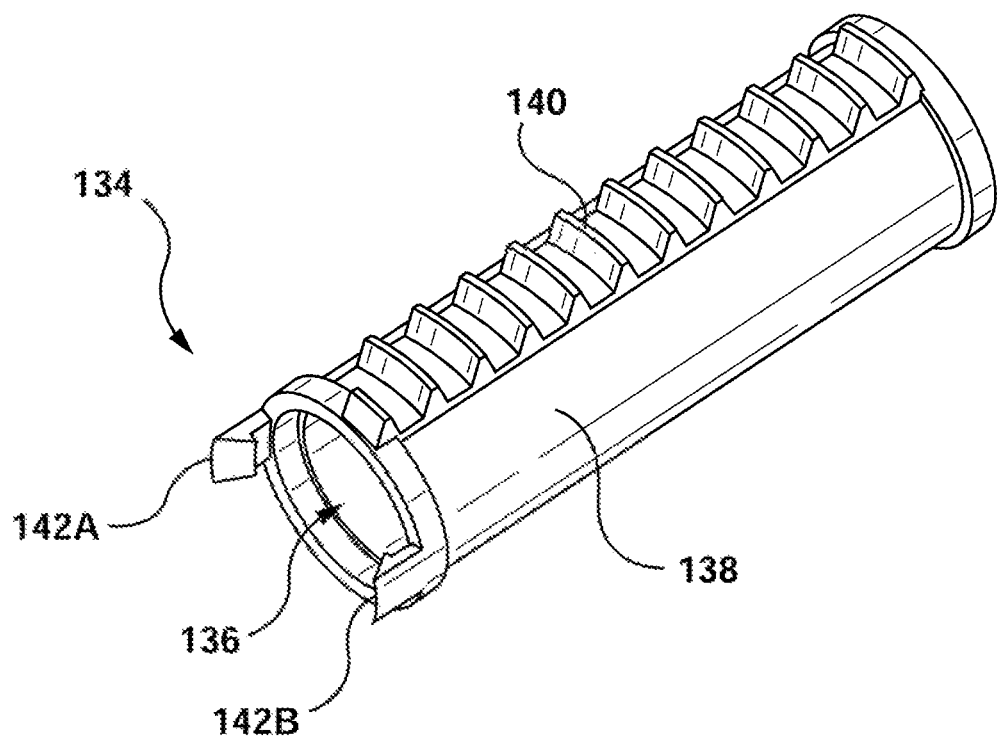
FIG. 12 is a perspective view of a rack of the handle of the catheter of FIG. 1, wherein the rack is removed from the handle for illustrative purposes.
Figure 15:
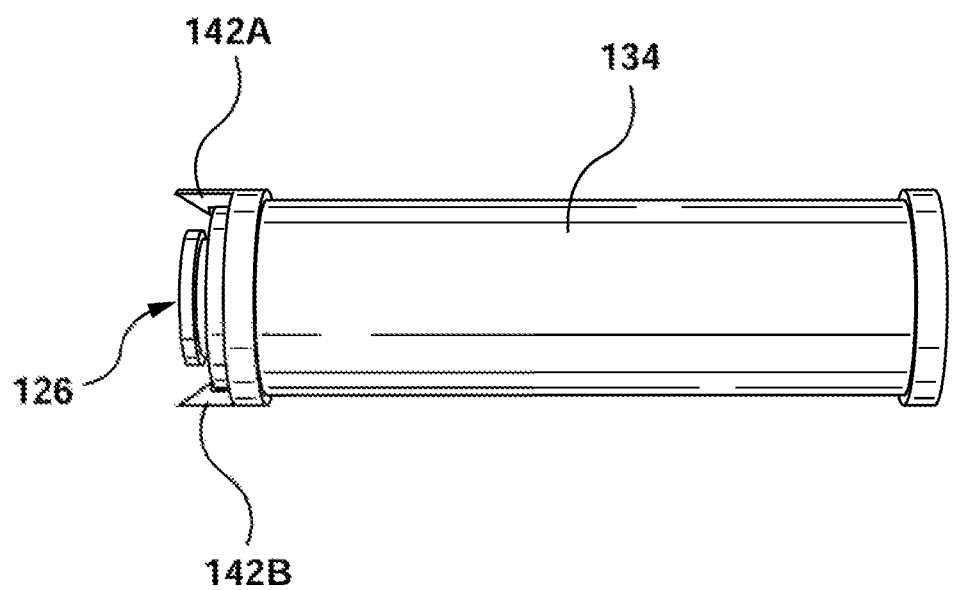
FIG. 15 is a side view of an assembly of the rack and the bearing of the handle of the catheter of FIG. 1, wherein the assembly is removed from the handle for illustrative purposes.

FIG. 12 illustrates a perspective view of the rack 134 removed from the handle 112 for illustrative purposes only. The rack 134 is a tubular component defining a lumen 136 therethrough such that the shaft 102 extends through the rack 134. The rack 134 is disposed within an interior of the housing 114 of the handle 112. The rack 134 includes a series of protrusions 140 formed on an outer surface 138 thereof for interacting with the knob 152 as will be explained in more detail herein. The rack 134 also includes first and second tabs or clips 142A, 142B that distally extend from a distal end of the rack 134. The first and second clips 142A, 142B are disposed at circumferentially opposing locations of the rack 134, and serve to couple the rack 134 to the bearing 126 as best shown in FIG. 15 which is a side view of an assembly of the rack 134 and the bearing 126. As shown in FIG. 15, the rack 134 is disposed abutting against or directly adjacent to the bearing 126 with the bearing 126 distally extending or protruding from the distal end of the rack 134. The first and second clips 142A, 142B extend over the radial flange 130 and couple the bearing 126 to the rack 134 such that the bearing 126 is slidable therewith. However, when the bearing 126 rotates with the nosecone 118 as described above during actuation of the torqueing mechanism 116, the bearing 126 rotates relative to or spins freely within the rack 134. The first and second clips 142A, 142B thus couple the bearing 126 to the rack 134 such that the bearing 126 is slidable therewith while still permitting the bearing 126 to spin freely or rotate within the rack 145.

Figure 13:
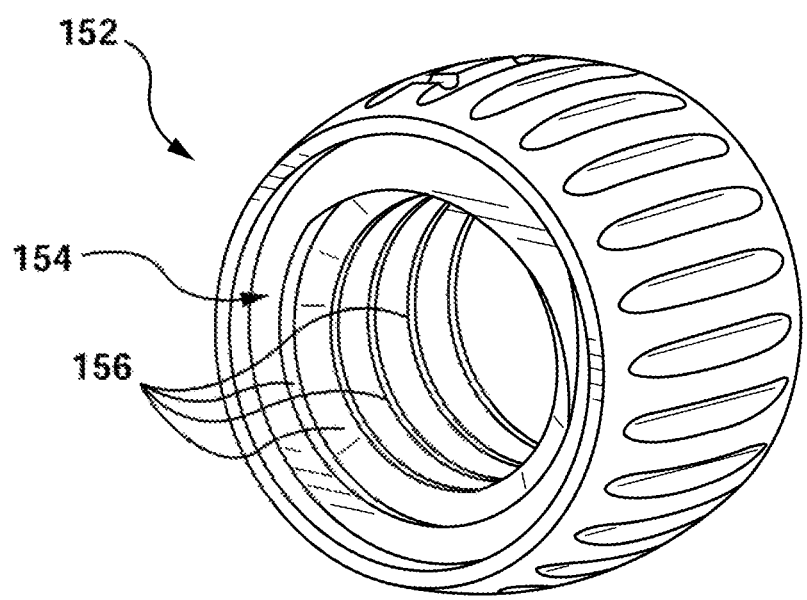
FIG. 13 is a perspective view of a knob of the handle of the catheter of FIG. 1, wherein the knob is removed from the handle for illustrative purposes.
Figure 14:
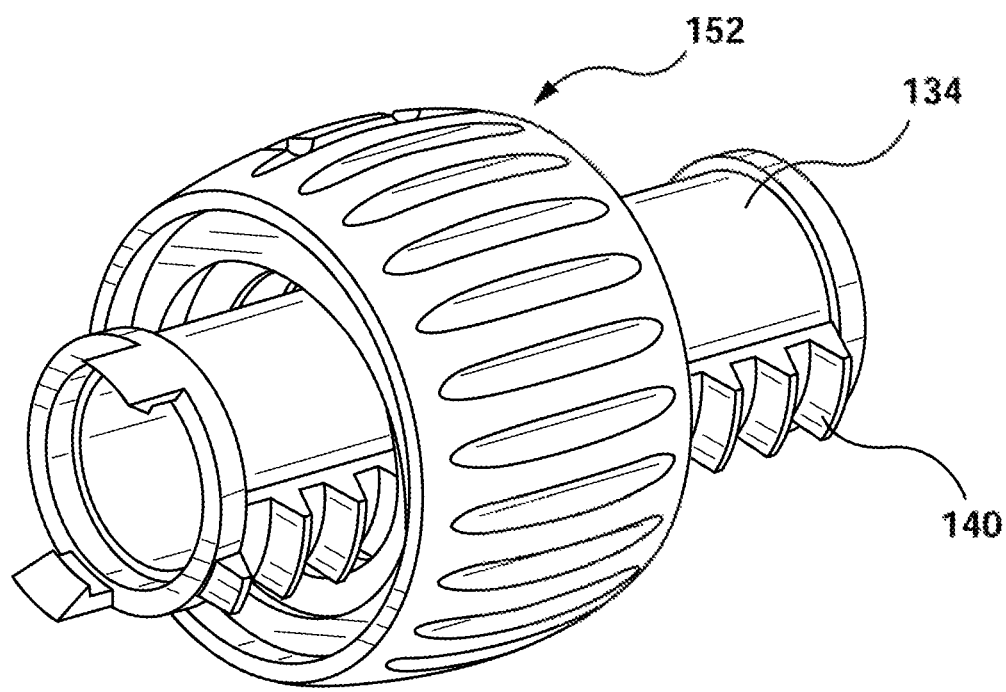
FIG. 14 is a perspective view of an assembly of the rack and the knob of the handle of the catheter of FIG. 1, wherein the assembly is removed from the handle for illustrative purposes.

FIG. 13 illustrates a perspective view of the knob 152 removed from the handle 112 for illustrative purposes only. The knob 152 is accessible and operable from an exterior of the housing 114. The knob 152 is concentrically disposed over the rack 134 as best shown in FIG. 14, which is a perspective view of an assembly of the rack 134 and the knob 152. The knob 152 includes a thread 156 on an inner surface 154 thereof that is configured to mate with or engage the series of protrusions 140 formed on the outer surface 138 of the rack 134. Stated another way, the threaded inner surface 154 of the knob 152 is threadedly engaged with the outer surface 138 of the rack 134. More particularly, thread 156 is a continuous helical ridge that wraps around the inner surface of the knob 152. Thread 156, sometimes called a continuous thread or a series of threads, has a rounded sinusoidal profile that mates with or engages the series of protrusions 140 formed on the outer surface 138 of the rack 134. As used herein, a rounded sinusoidal profile of thread 156 means that the continuous helical ridge that forms thread 156 has a rounded or smooth crown and the windings of the continuous helical ridge collectively have a sinusoidal or wavelike profile. In alternative embodiments, the threaded inner surface 138 of the knob 152 can be formed with other thread profiles which mate or engage with the series of protrusions 140 formed on the outer surface 138 of the rack 134.

Figure 16:
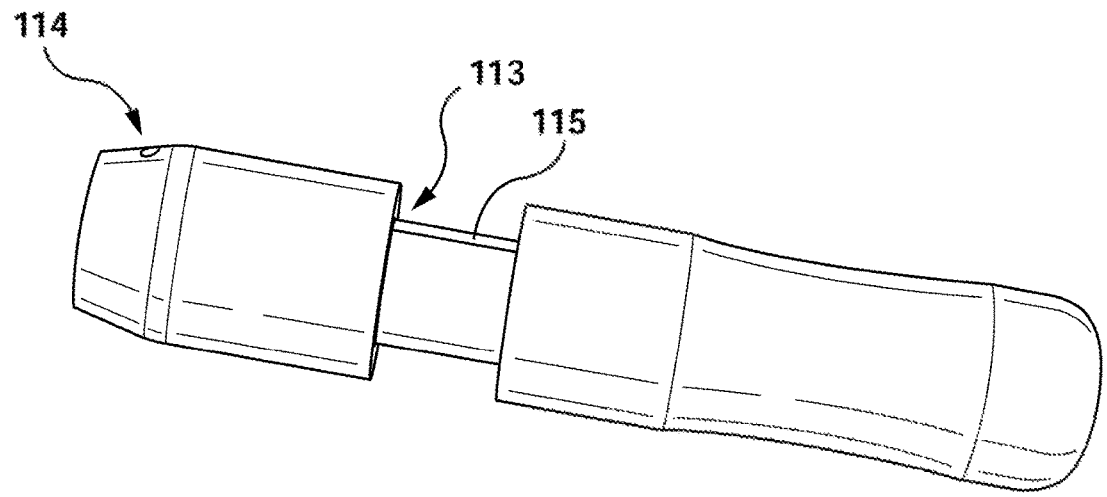
FIG. 16 is a perspective view of the housing or shell of the handle of the catheter of FIG. 1, wherein the housing is removed from the handle for illustrative purposes.
Figure 17:
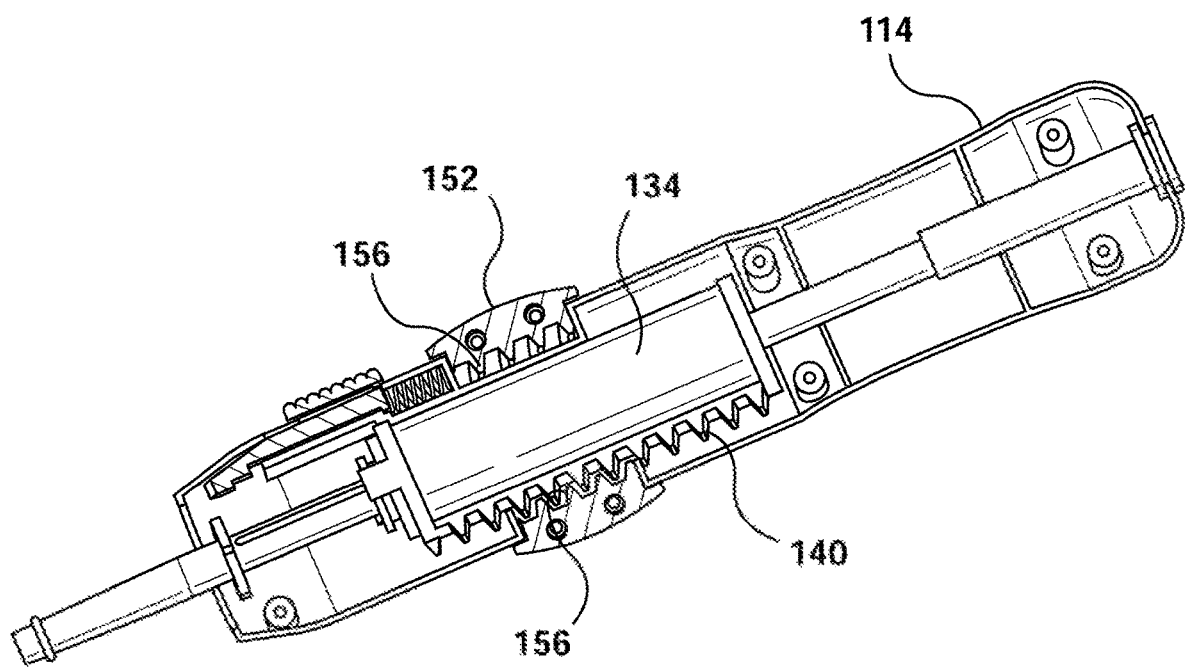
FIG. 17 is a side sectional view of the handle of the catheter of FIG. 1, wherein a portion of the housing and the nosecone are removed for illustrative purposes.

The thread 156 and the series of protrusions 140 formed on the outer surface 138 of the rack 134 are used to convert rotational movement to translational or linear movement. More particularly, the rack 134 is disposed within the housing 114 of the handle 112 such that the rack 134 is prevented from rotating relative to the housing 114. As shown in FIG. 16, the housing 114 includes a circumferential recess or groove 113 formed thereon that is configured to receive the knob 152. An opening 115 within the circumferential groove 113 is formed in a sidewall of the housing 114. The opening 115 permits interaction between the thread 156 formed on the inner surface 154 of the knob 152 and the series of protrusions 140 formed on the outer surface 138 of the rack 134 as best shown in the sectional view of FIG. 17. More particularly, the series of protrusions 140 formed on the outer surface 138 of the rack 134 extend radially outwards into the circumferential groove 113 of the housing 114 and mate or engage with the thread 156 of the knob 152. Further, since the series of protrusions 140 formed on the outer surface 138 of the rack 134 extend through the opening 115 of the housing 114, the walls of the housing 114 that form the opening 115 prevent the rack 134 from rotating relative to the housing 114. The walls of the housing 114 that form the opening 115 extend on either side of the series of protrusions 140 formed on the outer surface 138 of the rack 134, and thus act as a stop or barrier when the rack 134 attempts to rotate. As such, because the rack 134 is prevented from rotating relative to the housing 114 as explained above, and because the knob 152 also does not axially move due to being disposed within the circumferential groove 113 of the housing 114, the rotational movement of the knob 152 is converted to translational or linear movement of the rack 134 due to the threaded relationship between the thread 156 and the series of protrusions 140 formed on the outer surface 138 of the rack 134. When the knob 152 is rotated in a first direction, i.e., clockwise, the threaded relationship between the knob 152 and the rack 134 results in axial or longitudinal movement of the rack 134 in a proximal direction. Conversely, when the knob 152 is rotated in a second direction that opposes the first direction, i.e., counter-clockwise, the threaded relationship between the knob 152 and the rack 134 results in axial or longitudinal movement of the rack 134 in a distal direction.

Figure 18:
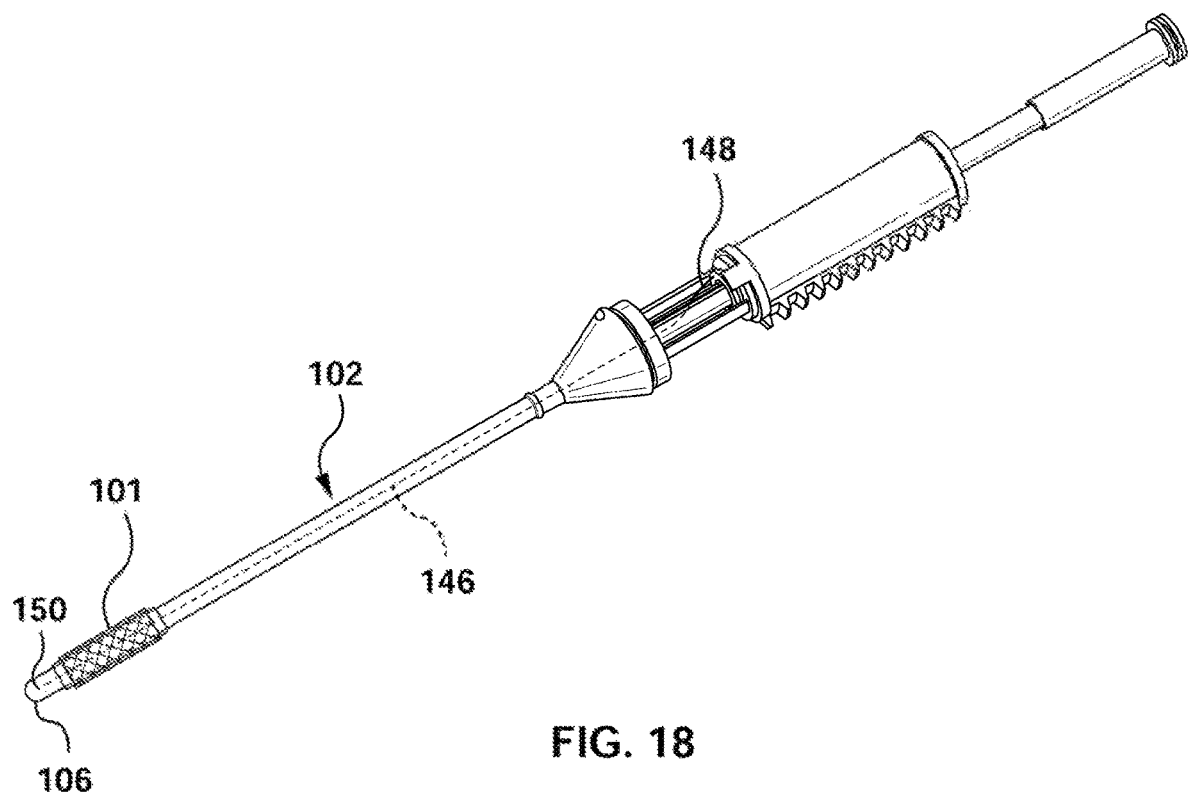
FIG. 18 is a perspective view of the catheter of FIG. 1, wherein the housing of the handle is removed for illustrative purposes and a pull wire of the steering mechanism is shown in phantom within the catheter.
Figure 19:
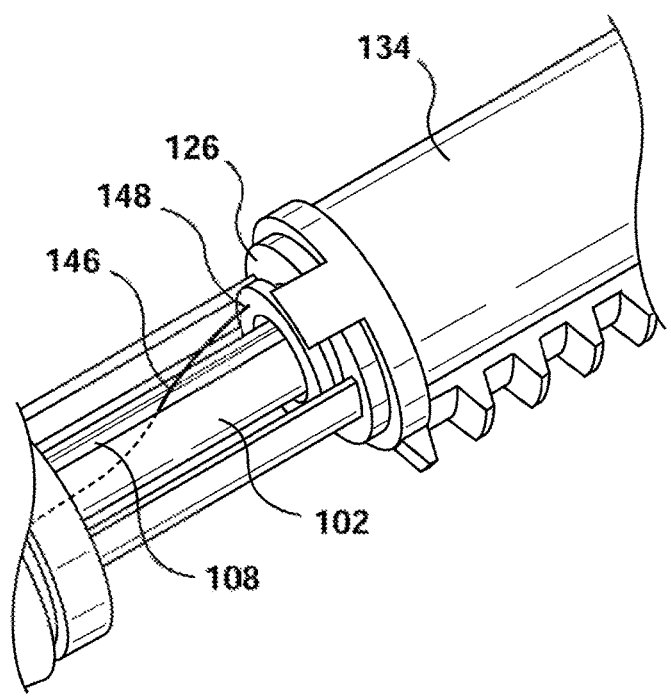
FIG. 19 is an enlarged view of a portion of FIG. 18, wherein the enlarged view depicts the pull wire exiting from the shaft and being attached to the bearing within the handle.

As the rack 134 is axially moved back and forth via rotation of the knob 152, the bearing 126 is slidable with the rack 134 over the shaft 102 via the first and second clips 142A, 142B described above with respect to FIG. 15. Further, the pull wire 146 is attached to the bearing 126. Thus, rotation of the knob 152 causes axial movement of the rack 134 and the bearing 126 coupled thereto, thereby tensioning the pull wire 146 to bend the distal portion of the shaft 102. More particularly, FIG. 18 illustrates a perspective view of the catheter 100 with the housing 114 of the handle 112 removed for illustrative purposes and with the pull wire 146 of the steering mechanism 144 shown in phantom within the catheter 100. The pull wire 146 has a proximal end 148 attached to the bearing 126 and a distal end 150 attached to a distal portion of the shaft 102. The pull wire 246 is disposed within the central lumen 110 of the shaft 102 and the pull wire 146 passes through the elongated slot 108 of the shaft 102 such that the proximal end 148 of the pull wire 146 is attached to the bearing 126 as best shown in FIG. 19, which an enlarged view of a portion of FIG. 18 that depicts the pull wire 146 exiting from the shaft 102 via the elongated slot 108. In an embodiment depicted herein, the pull wire 146 is formed from stainless steel and a metal band or ring (not shown) is utilized to attach the distal end 150 of the pull wire 146 to the shaft 102. The distal end 150 of the pull wire 146 is attached to the metal band by welding. In another embodiment hereof, the pull wire 146 is formed from KEVLAR or another relatively hard polymeric material and the polymer material of the distal end 150 is reflowed in order to attach the distal end 150 of the pull wire 146 to the shaft 102. The distal end 150 of the pull wire 146 may alternatively be attached to the shaft 102 using other conventional techniques, including bonding or adhesive, and it will be understood by one of ordinary skill in the art that the method of attachment depends upon the material of the pull wire 146.

The pull wire 146 is selectively tensioned via the steering mechanism 144 in order to bend the distal end 106 of the catheter. More particularly, rotation of the knob 152 causes axial movement of the rack 134 and the bearing 126 coupled thereto as described above. The bearing 126 slides relative to the shaft 102 and relative to the nosecone 118 during axial movement thereof. Since the pull wire 146 is attached to the bearing 126, axial movement of the rack 134 and the bearing 126 coupled thereto tensions the pull wire 146 to bend or curve the distal portion of the shaft 102. More particularly, when the bearing 126 and the pull wire 146 attached thereto are proximally retracted via the steering mechanism 144, the pull wire 146 is placed under tension and a distal portion of the shaft is curved to a radius of curvature. The dimension of the radius of curvature depends upon the intended application of the catheter 100, the target anatomy for use of the catheter 100, and/or the size or profile of the catheter 100. In an embodiment in which the catheter 100 is utilized in a transcatheter aortic valve implantation (TAVI) procedure, the radius of curvature ranges between twenty (20) millimeters and sixty (60) millimeters. In another embodiment hereof in which the catheter 100 is utilized in neurological applications, the radius of curvature may be as small as 0.5 centimeters. The steering mechanism 144 is accessible to a user via the handle 112 and the curvature of the distal portion of the catheter 100 can be changed based on the user manipulating the steering mechanism 144 via the knob 152 of the handle 112.

Notably, both the torqueing mechanism 116 and the steering mechanism 144 are integrated into the handle 112 such that operation of the torqueing mechanism 116 does not interfere with operation of the steering mechanism 144 and operation of the steering mechanism 144 does not interfere with operation of the torqueing mechanism 116. When the steering mechanism 144 is actuated via rotation of the knob 152, the rack 134 and the bearing 126 coupled thereto move axially or longitudinally relative to the shaft 102 and the nosecone 118 as described above without interfering with the torqueing mechanism. When the torqueing mechanism 116 is actuated via rotation of the nosecone 118, the bearing 126 rotates the shaft 102 and rotates relative to or spins freely within the rack 134 as described above without interfering with the steering mechanism 144. The pull wire 146 attached at its proximal end to the bearing 126 rotates to the same degree as the shaft 102 when the catheter 100 is being torqued via rotation of the nosecone 118.

Figure 20:
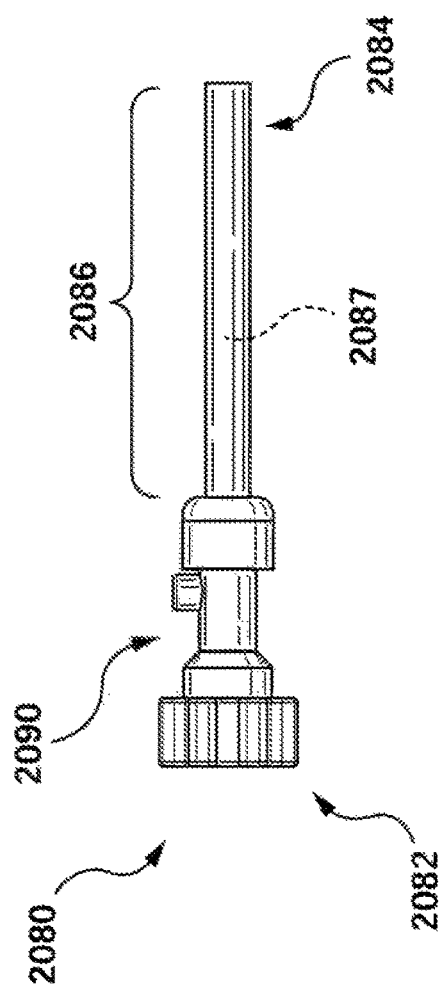
FIG. 20 is a side view of a valve relief component that may be utilized with the catheter of FIG. 1.

As previously described, a valve relief component may be utilized with the catheter 100. Turning now to FIG. 20, a side view of a valve relief component 2080 that may be utilized with catheter 100 is shown. The valve relief component 2080 includes a proximal end 2082 and a distal end 2084. A hub 2090 including a hemostasis valve or seal is disposed at the proximal end 2082 of the valve relief component 2080. The hemostasis valve or seal of the hub 2090 may be formed from a flexible material such as silicone and may include a lubricious coating such as parylene or silicone oil. The hemostasis valve or seal of the hub 2090 is configured to passively or actively seal against the shaft 102 when the shaft 102 is disposed therethrough, creating hemostasis.

Distally extending from the hub 2090 is a sheath 2086. The sheath 2086 is a tubular or cylindrical element defining a single lumen 2087 therethrough. The sheath 2086 is sized to be used with an introducer sheath with the lumen 2087 being sized or configured to slidingly receive the shaft 102 of the catheter 100, including the distal portion of the shaft 102 having the balloon-expandable prosthesis 101 disposed thereon. The sheath 2086 is of a sufficient length to cover or extend over the full or entire length of the balloon-expandable prosthesis 101 in its delivery or compressed configuration, and thus the particular length of the sheath 2086 may vary depending upon the application and length of the balloon-expandable prosthesis 101.

The sheath 2086 may be formed of one or more relatively rigid polymeric materials such as but not limited to nylon. Optionally, the sheath 2086 or some portion thereof may be formed as a composite having a reinforcement layer incorporated within a polymeric body in order to enhance strength and/or flexibility. Suitable reinforcement layers include braiding, wire mesh layers, embedded axial wires, embedded helical or circumferential wires, hypotubes, and the like. In one embodiment, for example, the entire length of the sheath 2086 is formed from a reinforced polymeric tube. In an embodiment, the sheath 2086 is translucent to allow visual inspection of the balloon-expandable prosthesis 101 when the sheath 2086 is disposed thereover. In another embodiment, the sheath 2086 may be opaque.

Figure 21:
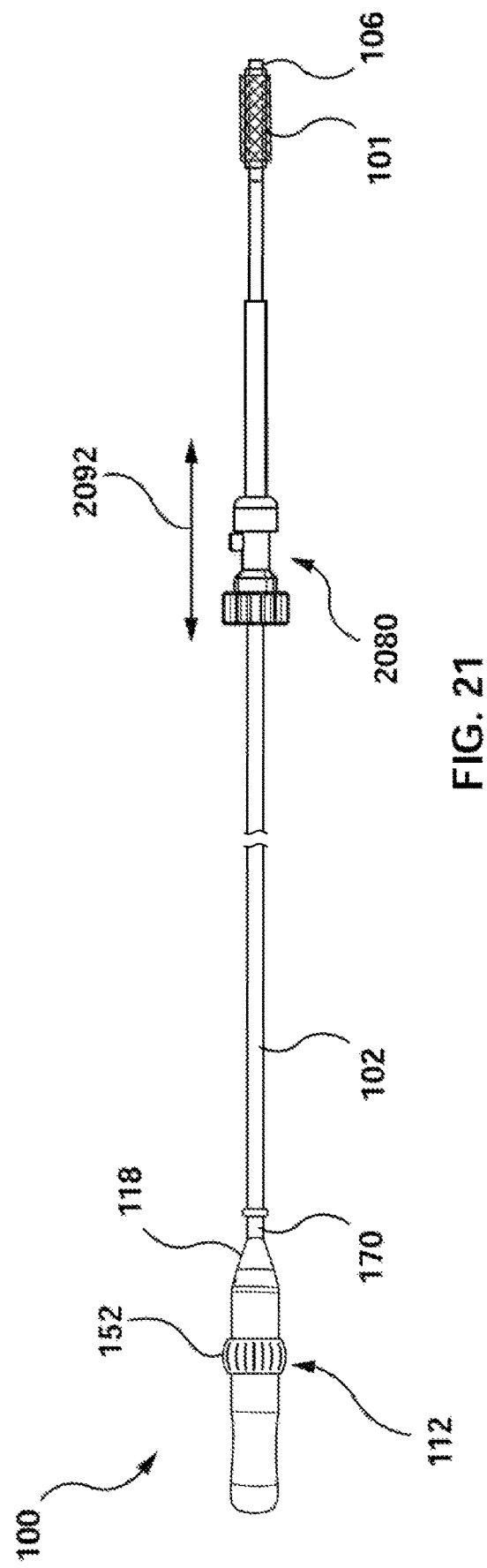
FIG. 21 is a side view of the valve relief component of FIG. 20 slidingly disposed over the shaft of the catheter of FIG. 1.
Figure 24:
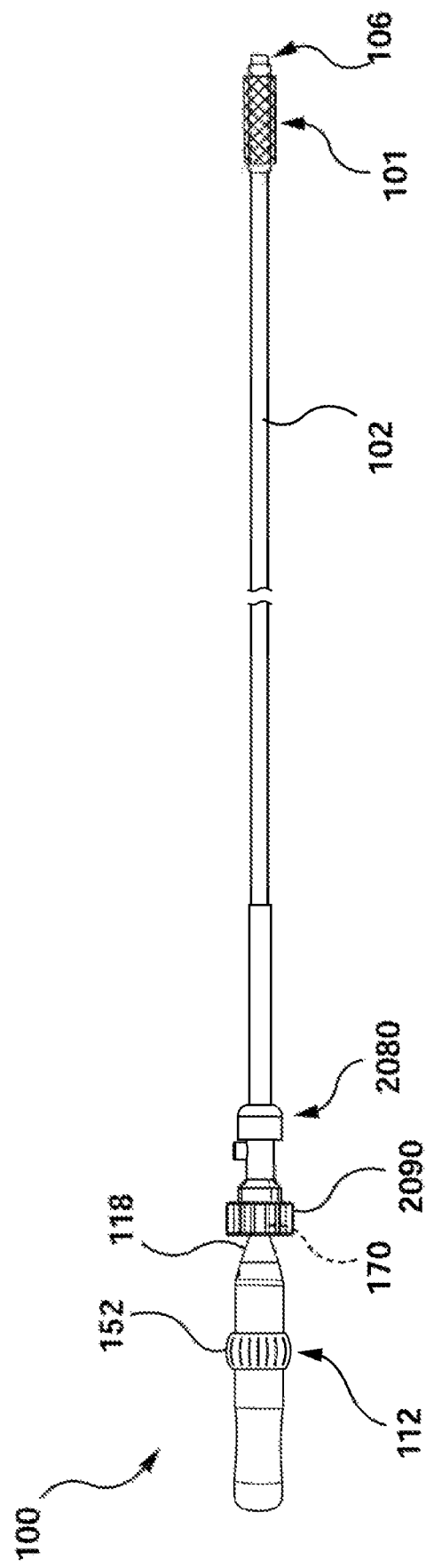
FIG. 24 is a side view of the catheter of FIG. 21, wherein the valve relief component of FIG. 20 is docked onto the strain relief component of the handle of the catheter.

FIG. 21 is a side view of the valve relief component 2080 slidingly disposed over the shaft 102 of the catheter 100. As previously described, the catheter 100 includes a handle 112, the shaft 102 distally extending from the handle 112, the strain relief component 170 concentrically disposed over a portion of the shaft 102 and distally extending from the handle 112, and the balloon-expandable prosthesis 101 disposed on a distal portion of the shaft 102. The valve relief component 2080 is slidingly disposed over an outer surface of the shaft 102. The valve relief component 2080 is slidable relative to the shaft 102 of the catheter 100 such that the valve relief component 2080 may be easily moved along the shaft 102 in a longitudinal direction as indicated by directional arrow 2092. As such, the valve relief component 2080 is configured to be selectively disposed over the balloon-expandable prosthesis 101 to protect the balloon-expandable prosthesis 101 during insertion into an introducer sheath (not shown on FIG. 21). More particularly, FIG. 22 is a side view of the distal portion of the catheter 100 with the sheath 2086 of the valve relief component 2080 disposed over the balloon-expandable prosthesis 101. When positioned over the balloon-expandable prosthesis 101, the valve relief component 2080 reduces or eliminates the external forces that the balloon-expandable prosthesis 101 experiences when loaded through a hemostatic valve of an introducer sheath, as shown in FIG. 23. FIG. 23 is a side view of the distal portion of the catheter 100 as the catheter is being inserted through a hub 2394 of an introducer sheath 2395 with the valve relief component 2080 disposed over the balloon-expandable prosthesis 101. The hub 2394 of the introducer sheath 2395 includes a hemostasis valve therein as well as a flush port 2396.

For example, in an embodiment, the balloon-expandable prosthesis 101 is a transcatheter aortic valve replacement prosthesis. When such a transcatheter aortic valve replacement prosthesis is inserted into the hub 2394 of an introducer sheath 2395, tissue of the transcatheter aortic valve replacement prosthesis comes in contact with the hemostasis valve of the hub 2394 of the introducer sheath 2395. The hemostasis valve of the hub 2394 of the introducer sheath 2395 may impart enough force on the transcatheter aortic valve replacement prosthesis to damage and/or displace the transcatheter aortic valve replacement prosthesis. However, when the valve relief component 2080 is positioned over the transcatheter aortic valve replacement prosthesis, the valve relief component 2080 protects the transcatheter aortic valve replacement prosthesis from damage or displacement by reducing or eliminating the external forces that the transcatheter aortic valve replacement prosthesis experiences when loaded through a hemostatic valve of the introducer sheath 2395.

After being advanced through the introducer sheath 2395, it is no longer required to have the valve relief component 2080 disposed over the balloon-expandable prosthesis 101 at the site of insertion. As such, the valve relief component 2080 is configured to dock onto the handle 112 of the catheter 100 as shown in the side view of the catheter 100 in FIG. 24. More particularly, the strain relief component 170 of the handle 112 of the catheter 100 is configured to serve as a docking station for the valve relief component 2080 when the valve relief component 2080 is not disposed over the balloon-expandable prosthesis 101. As described above with respect to FIGS. 8A and 8B, the distal end 176 of the strain relief component 170 extends or protrudes from a distal end of the housing 114 of the handle 112 and includes the raised ring 177. The valve relief component 2080 is secured or docked onto the raised ring 177 of the strain relief component 170 through an interference fit between the raised ring 177 and the inner surface of the valve relief component 2080. The torqueing mechanism 116 and the steering mechanism 144 may still be actuated via the nosecone 118 and the knob 152, respectively, when the valve relief component 2080 is docked or secured onto the strain relief component 170. After being docked onto the strain relief component 170, the valve relief component 2080 does not freely slide along the catheter 102 which may be bothersome to the user.

When performing a procedure, a guidewire (not shown) may be advanced intravascularly using any number of techniques and the introducer sheath 2395 is advanced along the guidewire. The catheter 100 is then loaded over the guidewire. The valve relief component 2080 is slid or moved longitudinally over the shaft 102 of the catheter until the sheath 2086 of the valve relief component 2080 covers the balloon-expandable prosthesis 101. With the valve relief component 2080 covering the balloon-expandable prosthesis 101, the valve relief component 2080 and the distal portion of the catheter 100 are distally advanced through the hub 2394 of the introducer sheath 2395. In an embodiment, the hub 2394 of the introducer sheath 2395 includes a stop (not shown) therein to alert the user that the valve relief component 2080 is inserted a sufficient depth into introducer sheath 2395. More particularly, the stop alerts the user that the balloon-expandable prosthesis 101 has entirely passed through the hemostasis valve of the introducer sheath 2395 and prevents the user from further inserting the valve relief component 2080. In an embodiment, the stop may be an integral flange or step formed on the inner surface of the hub 2394 of the introducer sheath 2395, the flange or step having a smaller diameter than an outer diameter of the valve relief component 2080. After the valve relief component 2080 contacts the stop within the hub 2394 of the introducer sheath 2395, the valve relief component 2080 may be slid along the shaft 102 in a proximal direction and be docked onto the strain relief component 170 of the handle 112 of the catheter 100.

Figure 25A:
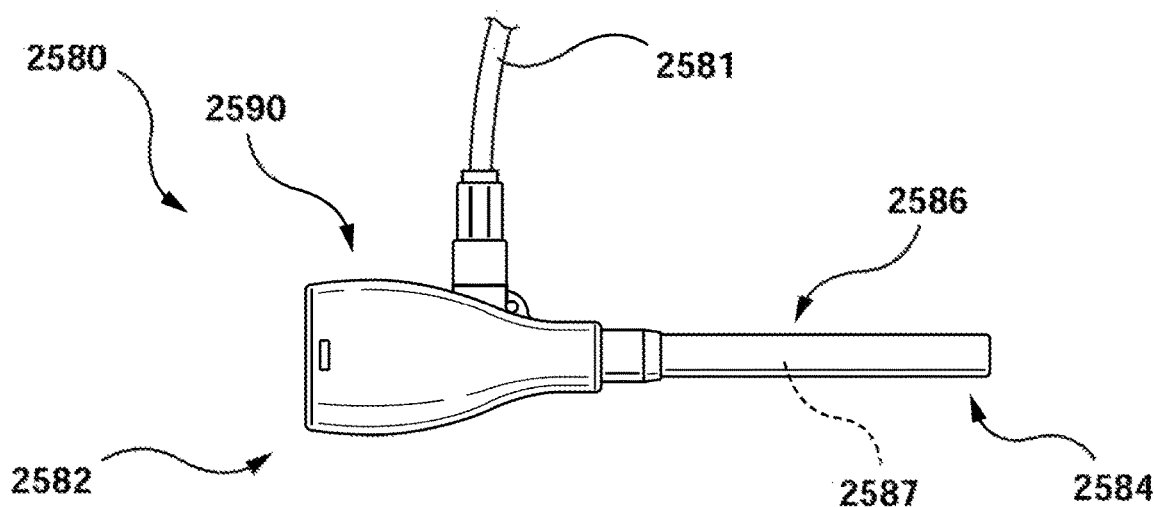
FIG. 25A is a side view of another configuration of a valve relief component that may be utilized with the catheter of FIG. 1.

FIG. 25A illustrates another embodiment of a valve relief component 2580 that may be utilized with catheter 100. Similar to the valve relief component 2080, the valve relief component 2580 includes a proximal end 2582 and a distal end 2584. A hub 2590 including a hemostasis valve or seal is disposed at the proximal end 2582 of the valve relief component 2580. A flush port 2581 is provided on the hub 2590. The hemostasis valve or seal of the hub 2590 may be formed from a flexible material such as silicone and may include a lubricious coating such as parylene or silicone oil. The hemostasis valve or seal of the hub 2590 is configured to passively or actively seal against the shaft 102 when the shaft 102 is disposed therethrough, creating hemostasis.

Distally extending from the hub 2590 is a sheath 2586. The sheath 2586 is a tubular or cylindrical element defining a single lumen 2587 therethrough. The sheath 2586 is sized to be used with an introducer sheath with the lumen 2587 being sized or configured to slidingly receive the shaft 102 of the catheter 100, including the distal portion of the shaft 102 having the balloon-expandable prosthesis 101 disposed thereon. The sheath 2586 is of a sufficient length to cover or extend over the full or entire length of the balloon-expandable prosthesis 101 in its delivery or compressed configuration, and thus the particular length of the sheath 2586 may vary depending upon the application and length of the balloon-expandable prosthesis 101.

The sheath 2586 may be formed of one or more relatively rigid polymeric materials such as but not limited to polyethylene. Optionally, the sheath 2586 or some portion thereof may be formed as a composite having a reinforcement layer incorporated within a polymeric body in order to enhance strength and/or flexibility. Suitable reinforcement layers include braiding, wire mesh layers, embedded axial wires, embedded helical or circumferential wires, hypotubes, and the like. In one embodiment, for example, the entire length of the sheath 2586 is formed from a reinforced polymeric tube. In this embodiment, the sheath 2586 is opaque. In another embodiment, the sheath 2586 is translucent to allow visual inspection of the balloon-expandable prosthesis 101 when the sheath 2586 is disposed thereover.

Figure 25B:
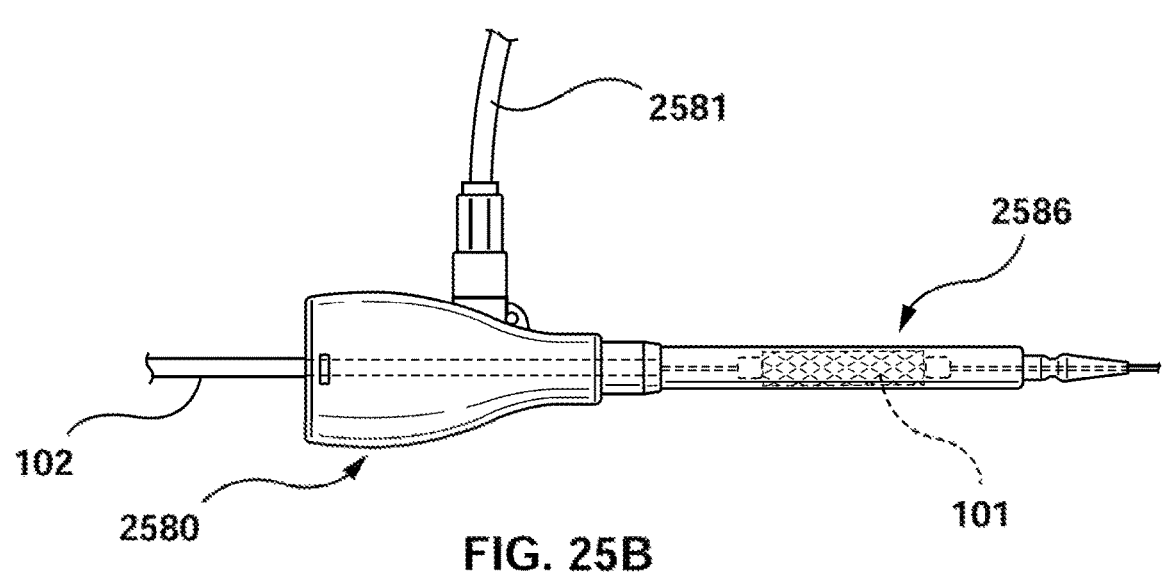
FIG. 25B is a side view of the distal portion of the catheter of FIG. 1, wherein the valve relief component of FIG. 25 is disposed over the balloon-expandable prosthesis.
Figure 25C:
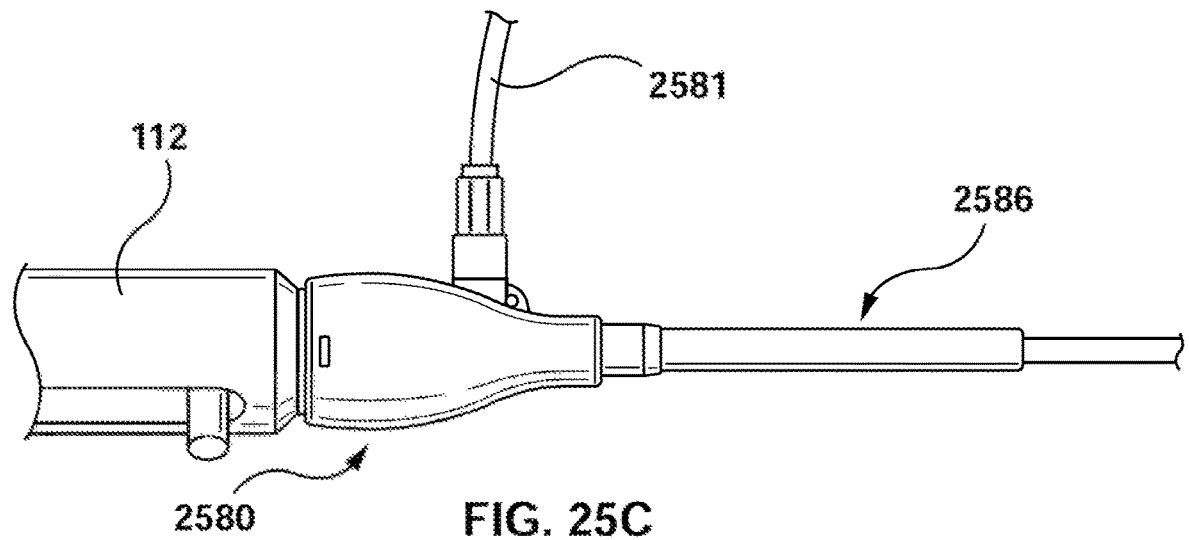
FIG. 25C is a side view of the distal portion of the catheter of FIG. 21, wherein the valve relief component of FIG. 25 is docked onto the strain relief component of the handle of the catheter.

Similar to the valve relief component 2080, the valve relief component 2580 is slidable relative to the shaft 102 of the catheter 100 such that the valve relief component 2580 may be easily moved along the shaft 102 in a longitudinal direction. As such, the valve relief component 2580 is configured to be selectively disposed over the balloon-expandable prosthesis 101 to protect the balloon-expandable prosthesis 101 during insertion into an introducer sheath. More particularly, FIG. 25B is a side view of the distal portion of the catheter 100 with the sheath 2586 of the valve relief component 2580 disposed over the balloon-expandable prosthesis 101. When positioned over the balloon-expandable prosthesis 101, the valve relief component 2580 reduces or eliminates the external forces that the balloon-expandable prosthesis 101 experiences when loaded through a hemostatic valve of an introducer sheath as described above with respect to the valve relief component 2080.

After being advanced through an introducer sheath, it is no longer required to have the valve relief component 2580 disposed over the balloon-expandable prosthesis 101. As such, as described above with respect to the valve relief component 2080, the valve relief component 2580 is configured to dock onto the handle 112 of the catheter 100 as shown in the side view of the catheter 100 in FIG. 25C.

Figures 26, 27:
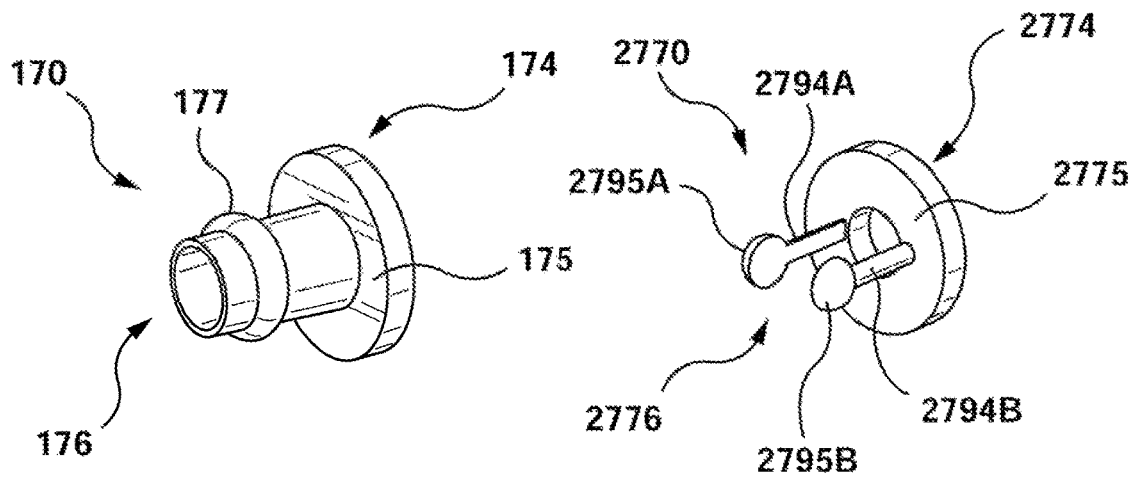
FIG. 26 is a perspective view of the strain relief component of the handle of the catheter of FIG. 1, wherein the strain relief component is removed from the catheter for illustrative purposes.
FIG. 27 is a perspective view of another configuration of a strain relief component that may be utilized in embodiments hereof.

The strain relief component 170 of the handle 112 of the catheter 100 is shown removed from the catheter for illustrative purposes in FIG. 26. As described above, the strain relief component 170 is a relatively short tubular component that defines a lumen therethrough that extends from the proximal end 174 to the distal end 176 thereof. The proximal end 174 includes the radial flange 175 that is configurated to attach to the interior of the nosecone 118 (not shown in FIG. 26). The distal end 176 of the strain relief component 170 extends or protrudes from a distal end of the housing 114 of the handle 112 and includes the raised ring 177 that is configured to provide an interference fit with the valve relief component 2080, 2580. The valve relief component 2080, 2580 is disposed over the tubular body of the strain relief component 170 with the raised ring 177 contacting an inner surface of the valve relief component 2080, 2580. As described herein, the strain relief component 170 is configured to serve as a docking station for the valve relief component 2080, 2580 when the valve relief component 2080, 2580 is not disposed over the balloon-expandable prosthesis 101. The valve relief component 2080, 2580 is secured or docked onto the raised ring 177 of the strain relief component 170 through an interference fit.

The strain relief component 170 may have alternative configurations to receive and secure the valve relief component 2080, 2580 thereon. For example, a strain relief component 2770 that may be used in embodiments hereof is shown in FIG. 27. The strain relief component 2770 has a proximal end 2774 and a distal end 2776 thereof. The proximal end 2774 includes the radial flange 2775 that is configurated to attach to the interior of the nosecone 118 (not shown in FIG. 27). First and second tabs 2794A, 2794B distally extend or protrude from the radial flange 2775. First and second tabs 2794A, 2794B each include a rounded tip 2795A, 2795B, respectively, at a distal end thereof that are configured to provide an interference fit with the valve relief component 2080, 2580. The valve relief component 2080, 2580 is disposed over the first and second tabs 2794A, 2794B with the rounded tips 2795A, 2795B contacting an inner surface of the valve relief component 2080, 2580. The strain relief component 2770 is configured to serve as a docking station for the valve relief component 2080, 2580 when the valve relief component 2080, 2580 is not disposed over the balloon-expandable prosthesis 101. The valve relief component 2080, 2580 is secured or docked onto the first and second tabs 2794A, 2794B of the strain relief component 2770 through an interference fit with the rounded tips 2795A, 2795B. The strain relief component 2770 is configured to be concentrically disposed over a portion of the shaft 102 at a distal end of the housing 114 and configured to function to relieve stress from the shaft 102 as it exits from the distal end of the housing 114.

Figures 28, 29:
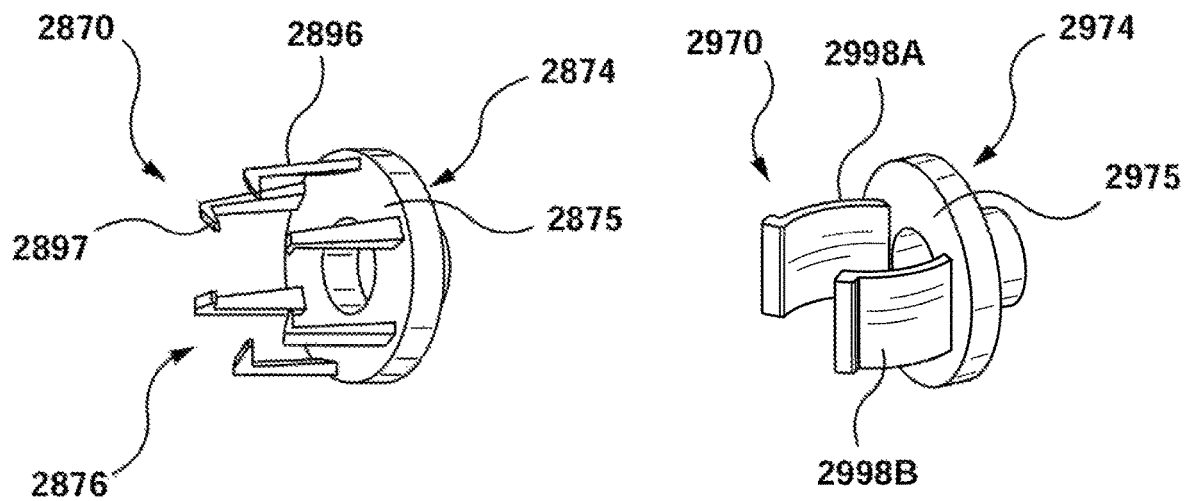
FIG. 28 is a perspective view of another configuration of a strain relief component that may be utilized in embodiments hereof.
FIG. 29 is a perspective view of another configuration of a strain relief component that may be utilized in embodiments hereof.

In another example, a strain relief component 2870 that may be used in embodiments hereof is shown in FIG. 28. The strain relief component 2870 has a proximal end 2874 and a distal end 2876 thereof. The proximal end 2874 includes the radial flange 2875 that is configured to attach to the interior of the nosecone 118 (not shown in FIG. 28). A plurality of prongs 2896 distally extend or protrude from the radial flange 2875 and are configured to receive the valve relief component 2080, 2580. Each prong 2896 includes a tang 2897 that extends radially inward at a distal end thereof. The valve relief component 2080, 2580 is disposed within the prongs 2896, with the tangs 2897 contacting an outer surface of the valve relief component 2080, 2580. The tangs 2897 are configured to provide an interference fit with the valve relief component 2080, 2580. The strain relief component 2870 is configured to serve as a docking station for the valve relief component 2080, 2580 when the valve relief component 2080, 2580 is not disposed over the balloon-expandable prosthesis 101. The valve relief component 2080, 2580 is secured or docked into the plurality of prongs 2896 of the strain relief component 170 through an interference fit with the tangs 2897 of the plurality of prongs 2896. The strain relief component 2870 is configured to be concentrically disposed over a portion of the shaft 102 at a distal end of the housing 114 and configured to function to relieve stress from the shaft 102 as it exits from the distal end of the housing 114.

In another example, a strain relief component 2970 that may be used in embodiments hereof is shown in FIG. 29. The strain relief component 2970 has a proximal end 2974 and a distal end 2976 thereof. The proximal end 2974 includes the radial flange 2975 that is configured to attach to the interior of the nosecone 118 (not shown in FIG. 29). First and second planar spring elements 2998A, 2998B distally extend or protrude from the radial flange 2975 and are configured to receive the valve relief component 2080, 2580. First and second planar spring elements 2998A, 2998B are each shape set into the configuration shown on FIG. 29, and resiliently return to their shape set configuration after deformation. The valve relief component 2080, 2580 is disposed within the first and second planar spring elements 2998A, 2998B, with the first and second planar spring elements 2998A, 2998B contacting an outer surface of the valve relief component 2080, 2580. The first and second planar spring elements 2998A, 2998B are configured to provide an interference fit with the valve relief component 2080, 2580. The strain relief component 2970 is configured to serve as a docking station for the valve relief component 2080, 2580 when the valve relief component 2080, 2580 is not disposed over the balloon-expandable prosthesis 101. The valve relief component 2080, 2580 is secured or docked into the first and second planar spring elements 2998A, 2998B of the strain relief component 170 through an interference fit therewith. The strain relief component 2970 is configured to be concentrically disposed over a portion of the shaft 102 at a distal end of the housing 114 and configured to function to relieve stress from the shaft 102 as it exits from the distal end of the housing 114.

Figure 30:
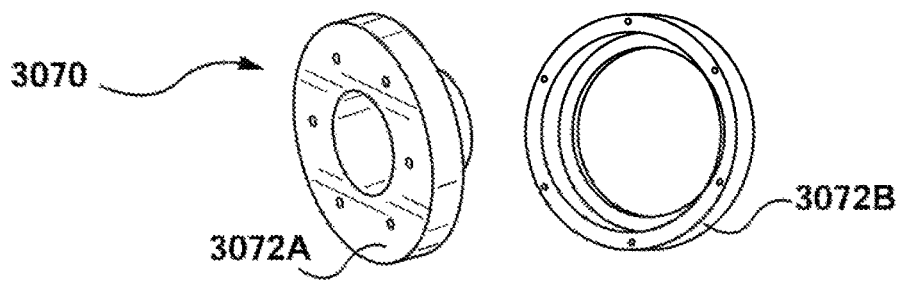
FIG. 30 is a perspective view of a magnetic coupling that may be utilized in embodiments hereof.

FIG. 30 is a perspective view of another configuration of a magnetic coupling that may be utilized in embodiments hereof in order to couple the valve relief component 2080, 2580 to the housing 114 of the handle 112. More particularly, a magnetic coupling 3070 includes first and second magnetic components 3072A, 3072B, respectively. The first magnetic component 3072A is attached to the proximal end 2082, 2582 of the valve relief component 2080, 2580, respectively, and the second magnetic component 3072B is attached to a distal end of the housing 114 of the handle 112. The first and second magnetic components 3072A, 3072B are operable to selectively and temporarily couple the valve relief component 2080, 2580 and the handle 112 together. Coupling between the valve relief component 2080, 2580 and the handle 112 is selectively achieved by means of the magnetic force between first and second magnetic components 3072A, 3072B. Both first and second magnetic components 3072A, 3072B may be formed from a magnetic material, or one of first and second magnetic components 3072A, 3072B is formed from a magnetic material and the other is formed from a ferromagnetic material.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. For example, the handle having both torqueing and steering mechanisms may be utilized in any type of catheter device. The catheter device having such a handle may include the strain relief component and the valve relief components described herein, or may be used without the strain relief and valve relief components. Conversely, the strain relief component and the valve relief components described herein may be incorporated into any type of catheter device, including a catheter device having a handle without the torqueing and steering mechanisms described herein. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A system comprising:
    an introducer sheath including a first hemostasis valve disposed therein; and
    a catheter including
        a handle;
        a shaft distally extending from the handle;
        a strain relief concentrically disposed over a portion of the shaft and distally extending from the handle;
        a balloon disposed on a distal portion of the shaft;
        a balloon-expandable prosthesis disposed over the balloon; and
        a valve relief slidingly disposed over an outer surface of the shaft between a first position and a second position, wherein the valve relief includes a hub and a sheath, a proximal end of the valve relief sheath being coupled to the hub such that the valve relief sheath distally extends from the hub, the hub including a second hemostasis valve disposed therein that is configured to seal against the shaft when the shaft is disposed therethrough, the valve relief sheath in the first position being disposed directly over the balloon-expandable prosthesis to protect the balloon-expandable prosthesis during insertion into the introducer sheath, and the hub of the valve relief in the second position being disposed over a distal portion of the strain relief, wherein the strain relief is configured to serve as a docking station for the valve relief when the valve relief is not disposed over the balloon-expandable prosthesis, and wherein the valve relief sheath has a length that is configured to extend over an entire length of the balloon-expandable prosthesis when the balloon-expandable prosthesis is in a delivery configuration.

2. The system of claim 1, wherein the balloon-expandable prosthesis is a valve replacement prosthesis.

3. The system of claim 1, wherein the strain relief includes a distal portion that is configured to mate with the valve relief through an interference fit between the distal portion and the valve relief.

4. The system of claim 3, wherein the distal portion of the strain relief includes a circumferential bump.

5. The system of claim 3, wherein the distal portion of the strain relief includes a pair of tabs, each tab with a rounded tip.

6. The system of claim 3, wherein the distal portion of the strain relief includes a plurality of prongs, each prong with a tang that extends radially inward at a distal end thereof.

7. The system of claim 3, wherein the distal portion of the strain relief includes a pair of planar spring elements.

8. The system of claim 1, wherein the strain relief is a tubular component and includes a radial flange at a proximal end thereof, the radial flange being attached to an interior of the handle.

9. The system of claim 1, wherein when positioned over the balloon-expandable prosthesis, the valve relief reduces external forces that the balloon-expandable prosthesis experiences when loaded through the introducer sheath.

10. The system of claim 1, wherein the strain relief is configured to mate with the valve relief through a magnetic coupling.

11. The system of claim 1, wherein the handle includes a housing, a tubular component disposed within the housing and over the shaft, and a rack disposed within the housing and axially movable relative to the housing of the handle, and wherein the catheter further includes a pull wire having a proximal end attached to the tubular component and a distal end attached to a distal portion of the shaft, and wherein the tubular component is coupled to the rack such that the tubular component moves axially with the rack and is rotatable relative to the rack, and wherein axial movement of the rack tensions the pull wire to bend the distal portion of the shaft.

\* \* \* \* \*